(12) United States Patent
Ruan et al.

(10) Patent No.: US 11,446,449 B2
(45) Date of Patent: Sep. 20, 2022

(54) SAFETY PEN NEEDLE ASSEMBLY

(71) Applicant: Embecta Corp., Andover, MA (US)

(72) Inventors: Tieming Ruan, Belmont, MA (US);
Robert Banik, Edgewater, NJ (US);
Eliot Zaiken, Covington, GA (US);
Michael Vincent Quinn, East Hanover, NJ (US); Gary Searle, Norfolk, MA (US)

(73) Assignee: Embecta Corp., Andover, MA (US)

( * ) Notice: Subject to any disclaimer, the term of this patent is extended or adjusted under 35 U.S.C. 154(b) by 268 days.

(21) Appl. No.: 16/570,697

(22) Filed: Sep. 13, 2019

(65) Prior Publication Data
US 2020/0030549 A1 Jan. 30, 2020

Related U.S. Application Data

(62) Division of application No. 13/058,649, filed as application No. PCT/US2009/054001 on Aug. 17, 2009, now abandoned.
(Continued)

(51) Int. Cl.
*A61M 5/32* (2006.01)

(52) U.S. Cl.
CPC ............ *A61M 5/3272* (2013.01); *A61M 5/326* (2013.01); *A61M 2005/3247* (2013.01); *A61M 2005/3254* (2013.01); *A61M 2005/3267* (2013.01)

(58) Field of Classification Search
CPC .............. A61M 25/0618; A61M 5/321; A61M 2005/3247; A61M 2005/3254; A61M 2005/3267; A61M 5/326; A61M 5/3272
See application file for complete search history.

(56) References Cited

U.S. PATENT DOCUMENTS 4,804,372 A 2/1989 Laico et al.
4,894,055 A 1/1990 Sudnak
(Continued)

FOREIGN PATENT DOCUMENTS

EP 0513869 A2 11/1992
EP 1949926 A1 7/2008
(Continued)

*Primary Examiner* — William R Carpenter
(74) *Attorney, Agent, or Firm* — Greenberg Traurig, LLP; David J. Dykeman; Roman Fayerberg

(57) ABSTRACT

In one aspect, a safety pen needle assembly is provided herein which includes a hub with a needle fixed to the hub, the needle having a distal end, formed for insertion into a patient, and a proximal end. The assembly further includes a shield and a biasing member disposed between the hub and the shield configured to urge the shield distally. A protrusion extends from at least one of the hub and the shield with a channel being formed in at least the other of the hub and the shield. The channel is formed to accommodate the protrusion. The shield is movable from a first position to a second position. In the first position, the shield is spaced from the distal end of the needle such that the distal end of the needle is exposed. In the second position, the shield covers the distal end of the needle. The channel guides the protrusion as the shield moves from the first position to the second position. With this arrangement, a shield may be directed to move in a desired path with stability. In addition, the distal end of the needle may be initially exposed to permit visual confirmation of priming, while allowing the shield to cover a majority of the needle to minimize any needle-related anxiety.

5 Claims, 30 Drawing Sheets

Related U.S. Application Data

(60) Provisional application No. 61/089,335, filed on Aug. 15, 2008.

(56) References Cited

U.S. PATENT DOCUMENTS

| | | | |
|---|---|---|---|
| 4,911,706 A * | 3/1990 | Levitt | A61M 5/3275 604/263 |
| 4,917,673 A | 4/1990 | Coplin | |
| 4,927,019 A | 5/1990 | Haber et al. | |
| 4,932,940 A | 6/1990 | Walker et al. | |
| 4,985,021 A | 1/1991 | Straw et al. | |
| 5,026,356 A | 6/1991 | Smith | |
| 5,137,521 A | 8/1992 | Wilkins | |
| 5,242,401 A | 9/1993 | Colsky | |
| 5,267,977 A | 12/1993 | Feeney | |
| 5,292,314 A | 3/1994 | D'Alessio et al. | |
| 5,389,085 A | 2/1995 | D'Alessio et al. | |
| 5,429,612 A | 7/1995 | Berthier | |
| 5,472,430 A | 12/1995 | Vaillancourt et al. | |
| 5,549,558 A | 8/1996 | Martin | |
| 5,573,512 A | 11/1996 | van den Haak | |
| 5,795,336 A | 8/1998 | Romano et al. | |
| 5,885,249 A | 3/1999 | Irisawa | |
| 6,203,529 B1 | 3/2001 | Gabriel et al. | |
| 6,547,764 B2 | 4/2003 | Larsen et al. | |
| 7,001,364 B1 | 2/2006 | Farhi | |
| 7,179,255 B2 | 2/2007 | Lettice et al. | |
| 7,497,847 B2 | 3/2009 | Crawford et al. | |
| 8,177,745 B2 | 5/2012 | Brechbuehler et al. | |
| 2002/0004648 A1 | 1/2002 | Larsen et al. | |
| 2002/0010434 A1 | 1/2002 | Larsen et al. | |
| 2002/0193748 A1 | 12/2002 | Cocker et al. | |
| 2003/0014018 A1 | 1/2003 | Giambattista et al. | |
| 2003/0028171 A1 | 2/2003 | DeHarde | |
| 2003/0078546 A1 | 4/2003 | Jensen | |
| 2003/0149403 A1 | 8/2003 | Barker et al. | |
| 2004/0111064 A1 | 6/2004 | Asbaghi | |
| 2005/0059936 A1 * | 3/2005 | Fiser | A61M 5/3275 604/263 |
| 2005/0096598 A1 | 5/2005 | Crawford | |
| 2005/0159706 A1 | 7/2005 | Wilkinson et al. | |
| 2006/0189033 A1 | 8/2006 | Alheidt | |
| 2008/0177237 A1 | 7/2008 | Stonehouse et al. | |
| 2009/0024093 A1 | 1/2009 | Carrel et al. | |
| 2009/0069753 A1 | 3/2009 | Ruan et al. | |
| 2009/0254042 A1 | 10/2009 | Gratwohl et al. | |
| 2010/0114035 A1 * | 5/2010 | Schubert | A61B 5/1444 604/198 |
| 2011/0118667 A1 | 5/2011 | Zaiken et al. | |
| 2011/0319832 A1 | 12/2011 | Chun | |

FOREIGN PATENT DOCUMENTS

| | | |
|---|---|---|
| JP | H02-140138 | 5/1990 |
| JP | H06-304254 | 1/1994 |
| JP | 6-63050 U | 9/1994 |
| JP | 2001-054572 | 2/2001 |
| JP | 2001-502191 | 2/2001 |
| JP | 2001-137343 | 5/2001 |
| JP | 2001-231858 A | 8/2001 |
| JP | 2001-286562 | 10/2001 |
| JP | 2004-505663 | 2/2004 |
| JP | 2004-528939 | 9/2004 |
| JP | 2005-516691 A | 6/2005 |
| JP | 2005-253613 | 9/2005 |
| JP | 2006-175070 | 7/2006 |
| JP | 2008-220934 A | 9/2008 |
| JP | 2010-501295 | 1/2010 |
| JP | 2010-602316 A | 1/2010 |
| WO | 9301851 A1 | 2/1993 |
| WO | 9731666 | 9/1997 |
| WO | 0211635 | 2/2002 |
| WO | 02100467 A2 | 12/2002 |
| WO | 20070099367 A1 | 2/2006 |
| WO | 2006131832 A1 | 12/2006 |
| WO | 2008-025179 A1 | 3/2008 |
| WO | WO-2008028305 A1 | 3/2008 |
| WO | WO-2008097217 A1 | 8/2008 |

* cited by examiner

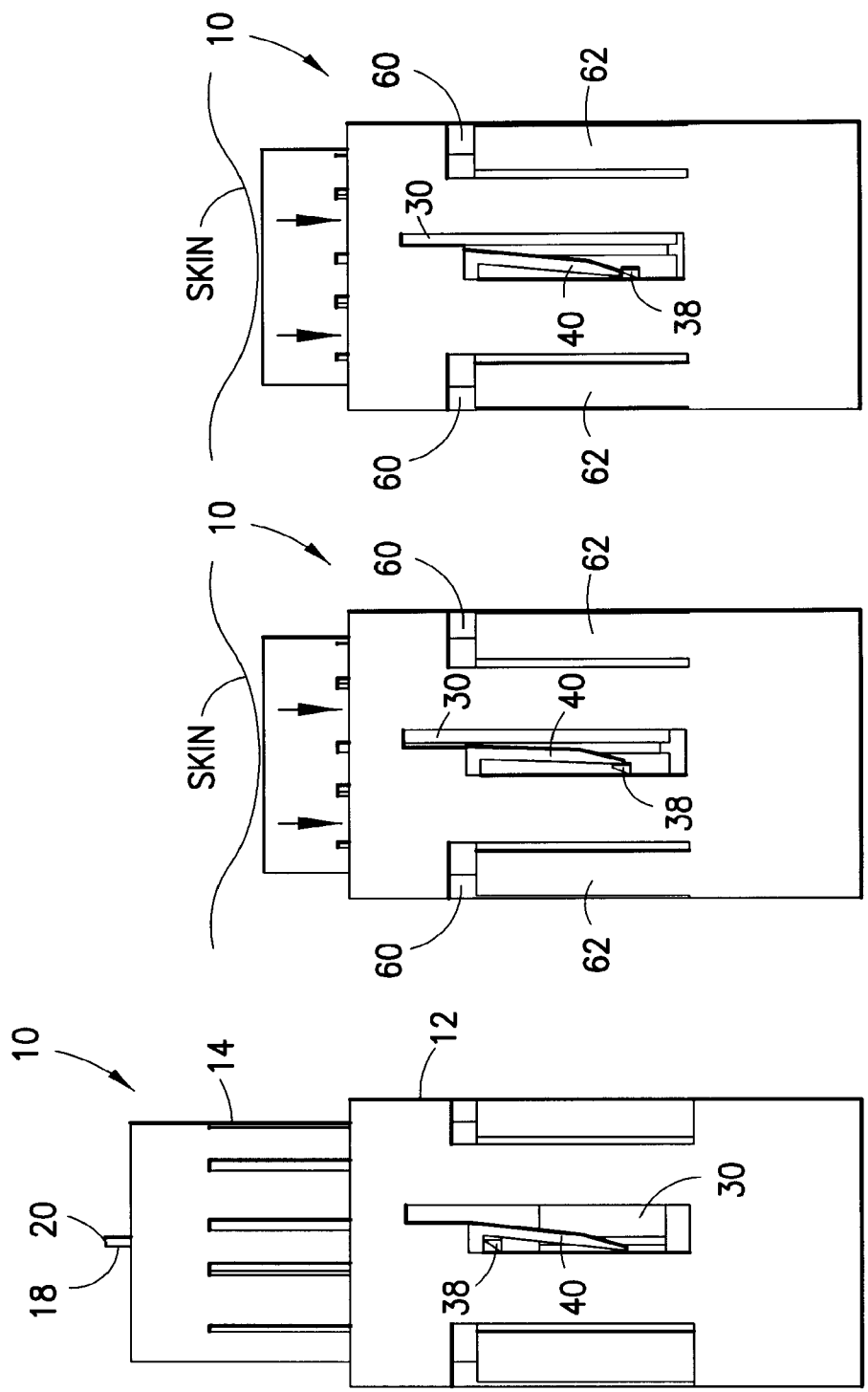

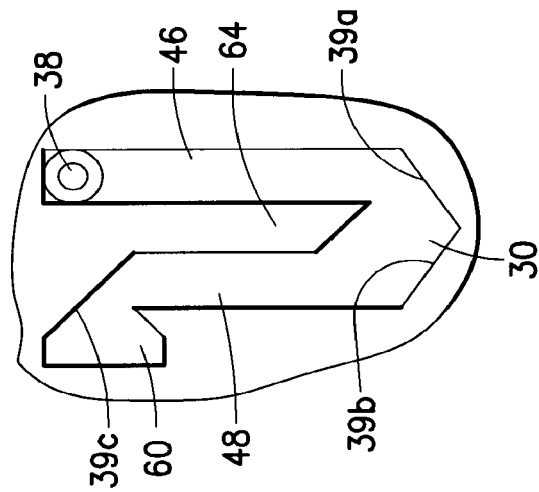
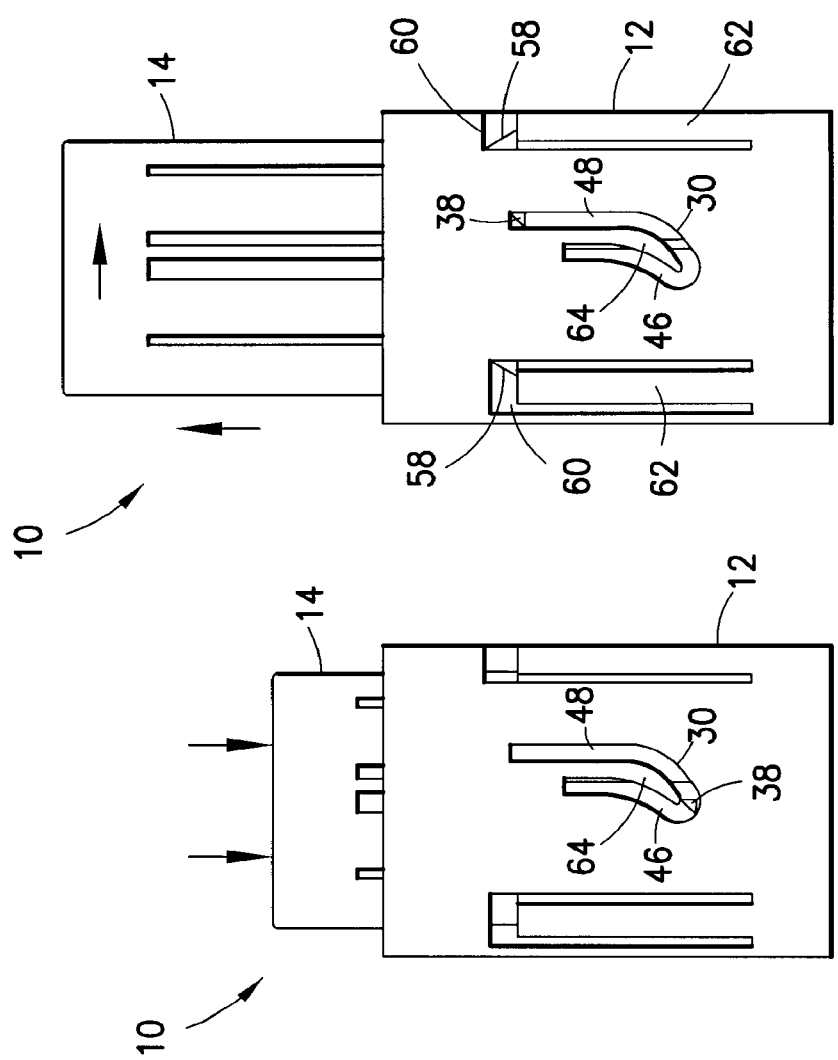

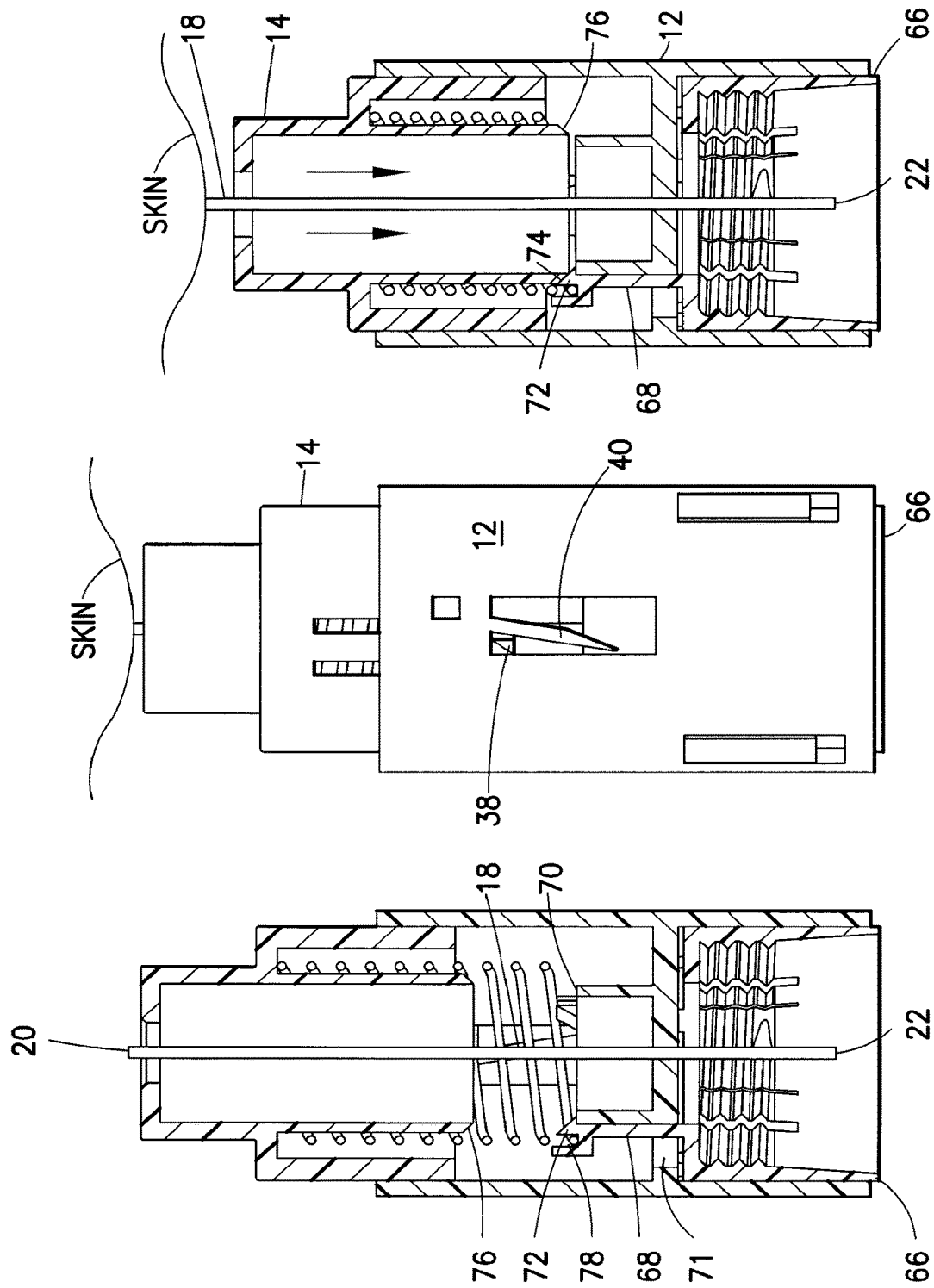

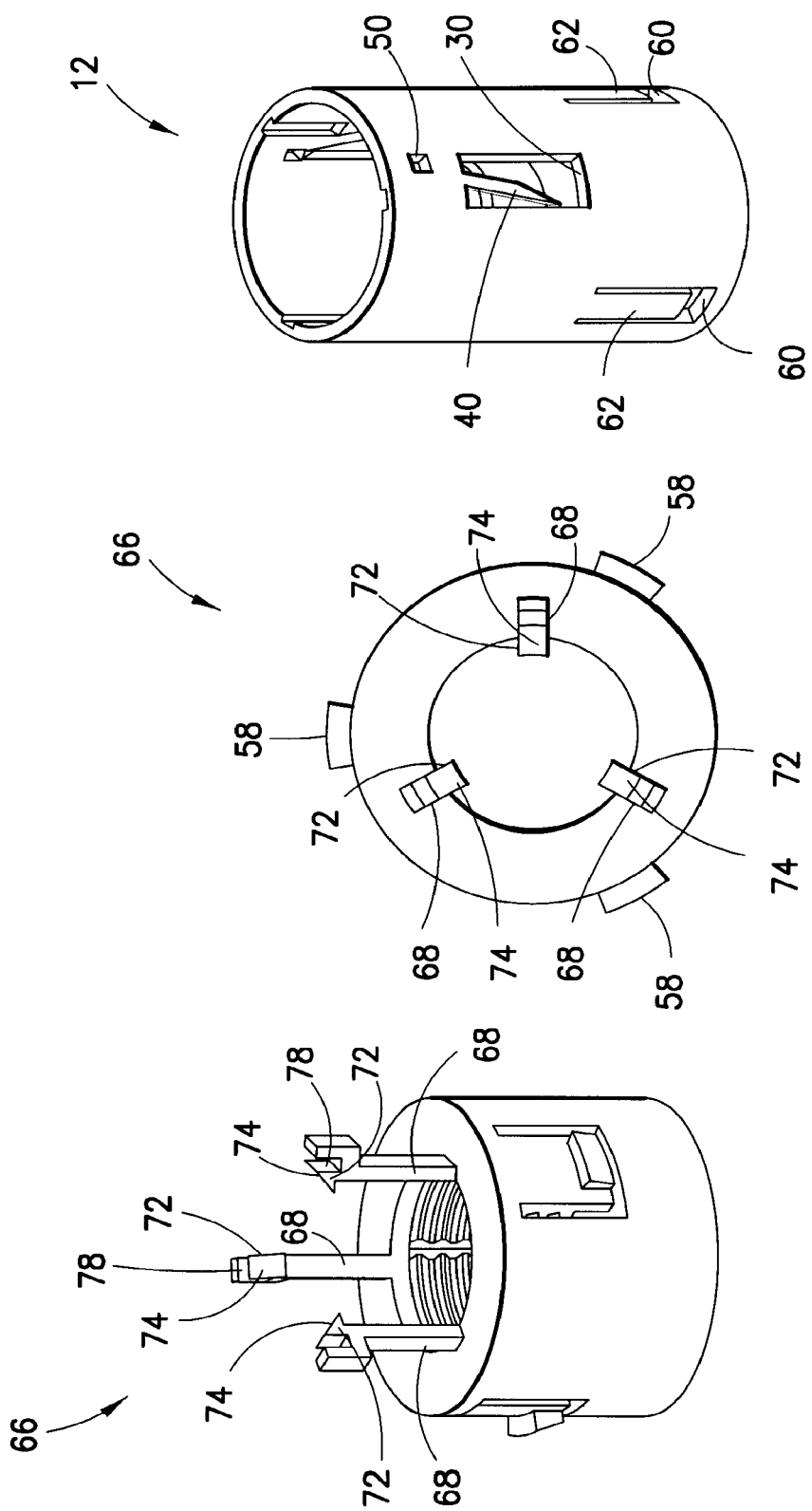

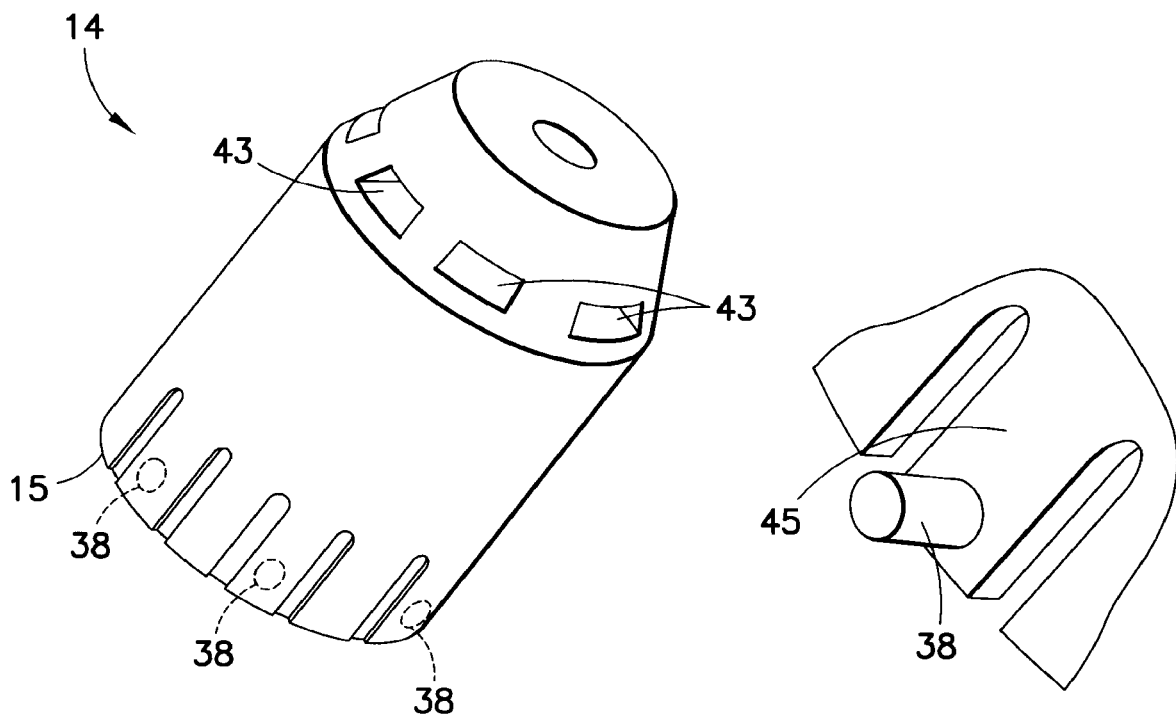
FIG.53
FIG.53A
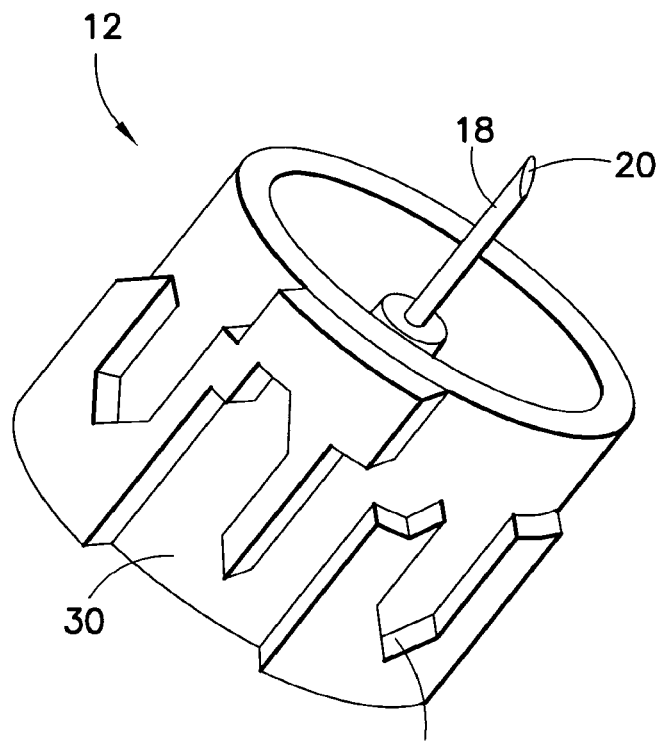
FIG.54

SAFETY PEN NEEDLE ASSEMBLY

RELATED APPLICATIONS

This application is a division of U.S. patent application Ser. No. 13/058,649, filed on Mar. 15, 2011, which is the U.S. national stage of International Patent Application No. PCT/US2009/054001, filed on Aug. 17, 2009, which claims priority from U.S. Provisional Application No. 61/089,335, filed on Aug. 15, 2008, the disclosures of all of which are incorporated herein by reference in their entirety.

BACKGROUND OF THE INVENTION

Safety pen needle assemblies are known in the prior art for providing shielding to a used pen needle to prevent inadvertent "needle sticks" therewith. These assemblies may be "passive", which operate through normal use of the associated pen injector, or "active", which require an additional step or steps to operate beyond normal operation of the associated pen injector.

Passive safety pen needle assemblies have been developed in the prior art which utilize a trigger that is activated upon sufficient application of force thereto during an injection procedure. A trigger may be provided which presses against a patient's skin with sufficient displacement of the trigger causing the assembly to activate. The activation of the trigger results in some form of a shield being released which may move distally to a shielding position covering a used needle. With these designs, concerns exist of preventing inadvertent trigger activation.

SUMMARY OF THE INVENTION

In one aspect, safety pen needle assembly is provided herein which includes a hub with a needle fixed to the hub, the needle having a distal end, formed for insertion into a patient, and a proximal end. The assembly further includes a shield and a biasing member disposed between the hub and the shield configured to urge the shield distally. A protrusion extends from at least one of the hub and the shield with a channel being formed in at least the other of the hub and the shield. The channel is formed to accommodate the protrusion. The shield is movable from a first position to a second position. In the first position, the shield is spaced from the distal end of the needle such that the distal end of the needle is exposed. In the second position, the shield covers the distal end of the needle. The channel guides the protrusion as the shield moves from the first position to the second position. With this arrangement, a shield may be directed to move in a desired path with stability. In addition, the distal end of the needle may be initially exposed to permit visual confirmation of priming, while allowing the shield to cover a majority of the needle to minimize any needle-related anxiety.

These and other features of the invention will be better understood through a study of the following detailed description and accompanying drawings.

BRIEF DESCRIPTION OF THE DRAWINGS

FIGS. 1-61 depict various safety pen needle assemblies, and components thereof, formed in accordance with the subject invention.

FIGS. 1-8 depict hubs or shields with channels that have moveable protrusions;

FIGS. 28-32 depict depicts hubs or shields with straight channels that allow shields to be manually rotated to a locking position;

FIGS. 33-35 depict a shield or hub with a locking window and a curved channel;

FIG. 35A depicts an alternative arrangement for a curved channel;

FIGS. 37-43 depict a safety pen assembly with a secondary shield on the proximal end with one or more locking arms;

FIGS. 44-45 depict a secondary shield with one or more locking arms;

FIGS. 46-48 depict a hub or shield with locking features for the secondary shield with one or more locking arms;

FIG. 53 depicts a shield with a plurality of integral protrusions and locking windows and FIG. 53A depicts an internal view of the integral protrusions of FIG. 53;

FIG. 54 depicts a hub with a plurality of channels;

FIGS. 60A-61 depict embodiments for determining the depth of the protrusion of a needle.

DETAILED DESCRIPTION OF THE INVENTION

Figures 1, 2:
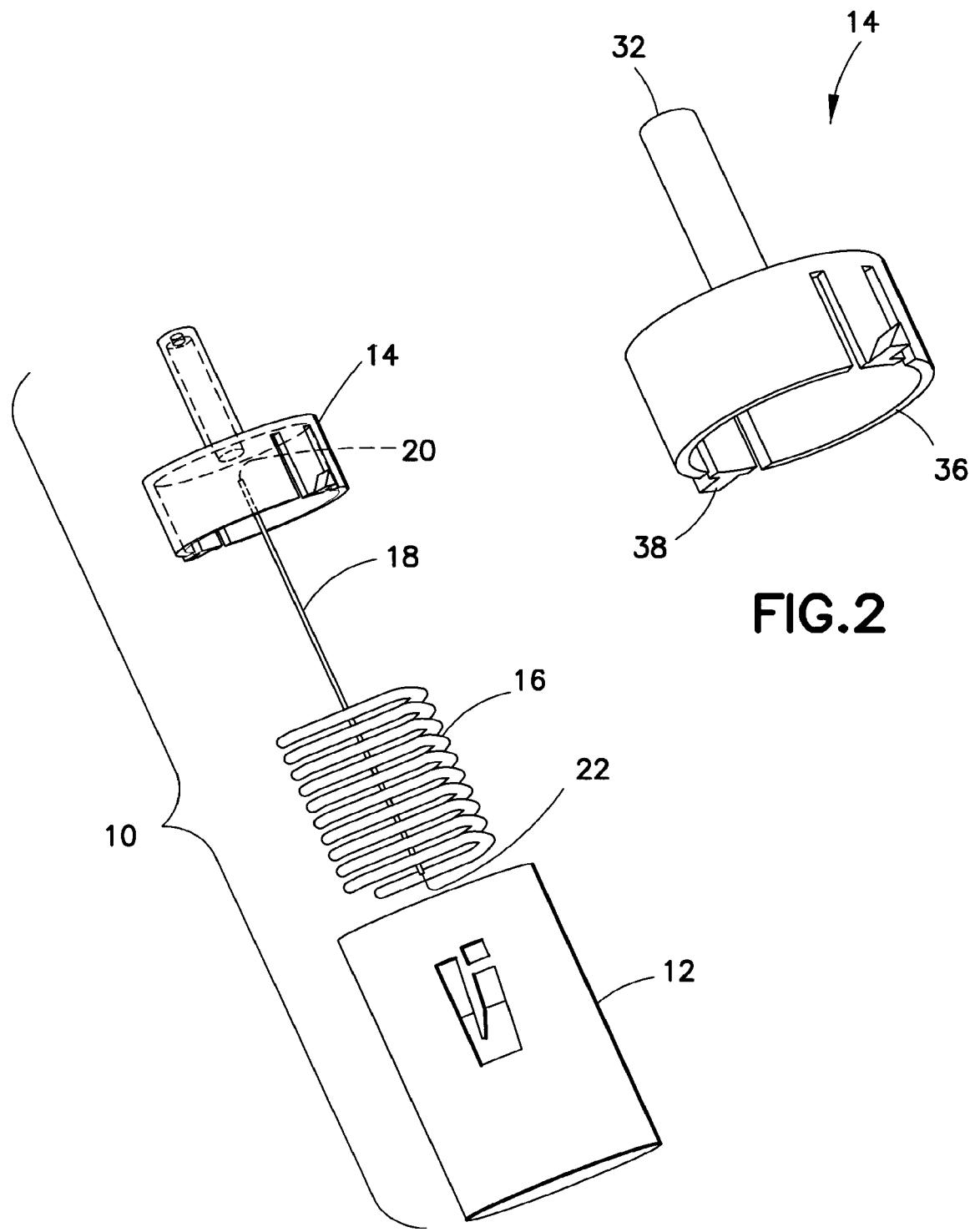
Figure 4:
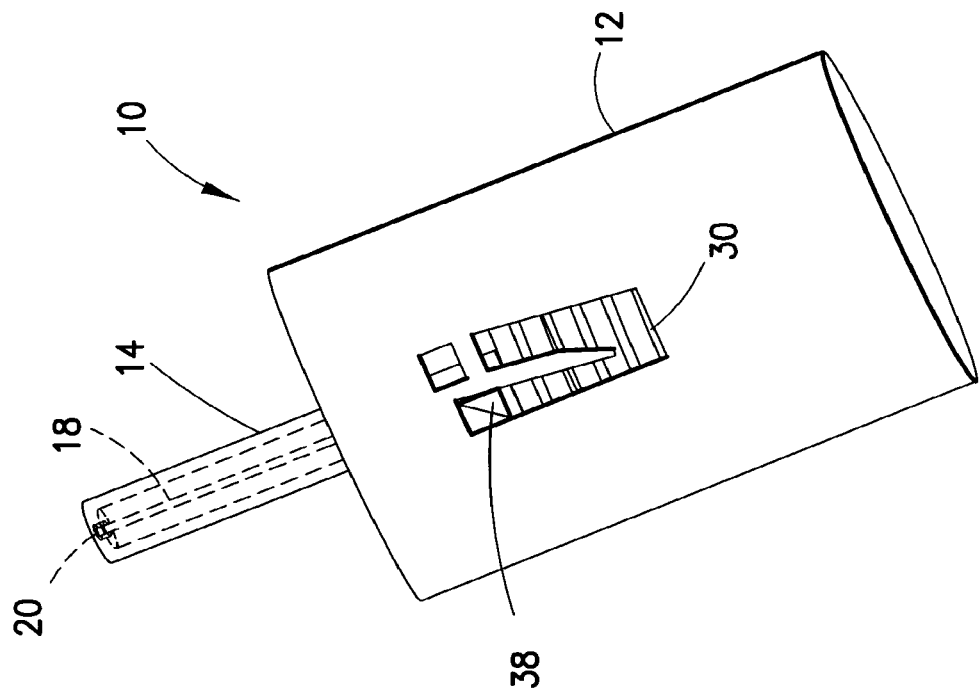
Figure 3:
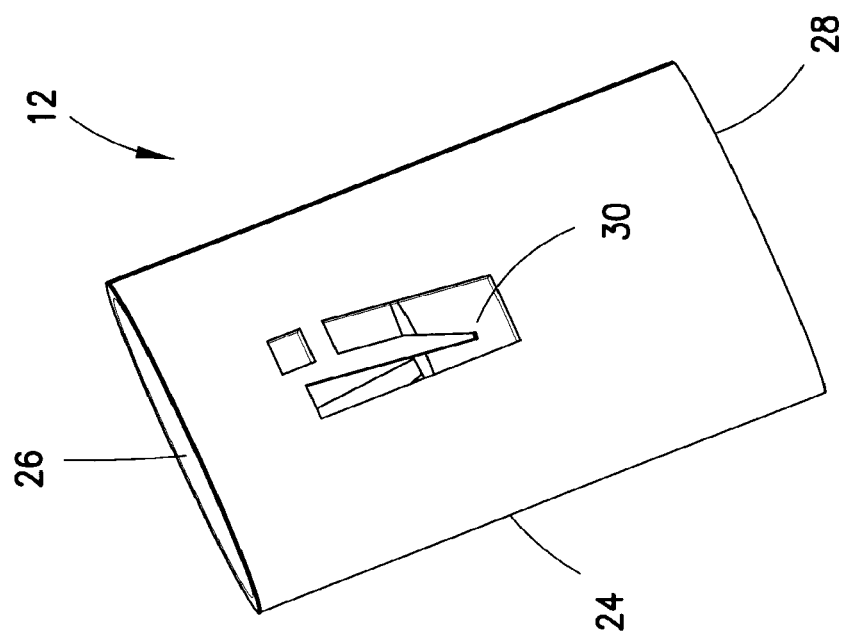
Figure 57A:
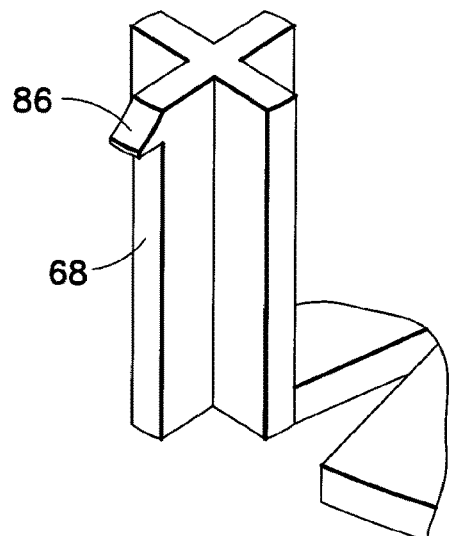
Figure 57B:
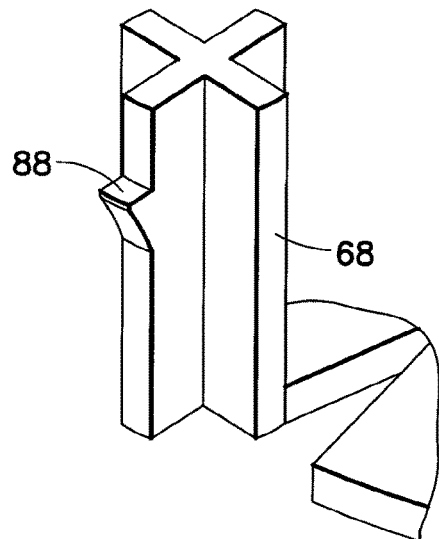

With reference to FIGS. 1-57B, a safety pen needle assembly 10 is shown which generally includes a hub 12, a shield 14, and a biasing element 16 located therebetween. A needle 18 having a distal end 20, formed for insertion into a patient during a medical injection, and a proximal end 22 is provided and fixed to the hub 12. The safety pen needle assembly 10 is configured to have the shield 14 cover the distal end 20 of the needle 18 after use, i.e., after an injection.

The hub 12 includes a generally tubular body 24 having spaced apart distal and proximal ends 26, 28. The tubular body 24, preferably in proximity to the proximal end 28, may be provided with a mounting arrangement (e.g., threads; luer) configured for mounting onto the body of a medical injector, e.g., a pen injector. A channel 30 is provided which may be formed in the hub 12 or the shield 14. With reference to FIGS. 1-8, the channel 30 may be formed in the tubular body 24 to generally extend in a longitudinal direction from the distal end 26 to the proximal end 28 of the tubular body 24. As shown in the figures, the channel 30 may be a throughhole, which extends completely through the wall of the tubular body 24, or may be "blind" and be of limited depth in the tubular body 24 without extending therethrough. The channel 30 may have various configurations. With reference to FIGS. 1-8, the channel 30 may have a hook-, U- V-, J- or L-shape.

The shield 14 includes a distal end 32, having an aperture 34 (FIG. 5) formed therethrough, and a proximal end 36. The shield 14 may be of various configurations, as will be appreciated by those skilled in the art.

A protrusion 38 may be provided on the hub 12 or the shield 14, formed to be accommodated in the channel 30. With reference to the embodiment of FIGS. 1-8, the protrusion 38 projects from the shield 14. The biasing element 16 is disposed to urge the shield 14 distally. Under force of the biasing element 16, the protrusion 38 is preferably urged to the distalmost portion of the channel 30. The interengagement of the protrusion 38 and the tubular body 24, at the end of the channel 30, limits distal movement of the shield 14 relative to the hub 12.

Prior to use, the shield 14 is configured to be in an initial pre-use state. In this pre-use state, the shield 14 may be configured to cover the distal end 20 of the needle 18 (FIG. 4) or may be configured to leave the distal end 20 exposed (FIG. 28). The initial state of coverage of the distal end 20 may be determined by user preference. With the distal end 20 being initially covered, the needle 18 is not visible, thereby minimizing anxiety, particularly for a needlephobe. Alternatively, with the distal end 20 being exposed, a user may visually confirm proper priming and needle placement during an injection. Even with the distal end 20 being exposed, a majority of the needle 18 may still be covered to minimize anxiety.

During use, the shield 14 is caused to move proximally while pressed against a patient's skin, against the force of the biasing element 16. With sufficient pressure, the needle 18, passing through the aperture 34, enters the patient's skin the required depth and an injection is administered as is well known in the art. The shield 14 is urged proximally during this procedure. During this proximal movement, the protrusion 38 is guided by the channel 30. After injection, and removal of the shield 14 from the patient, the biasing element 16 urges the shield 14 distally to a position where the distal end 20 of the needle 18 is covered. The safety pen needle assembly 10 may be provided with a locking arrangement to lock the shield 14 in the final, shielded position covering the distal end 20. As appreciated by those skilled in the art, various locking arrangements are useable with the subject invention.

Figure 6:
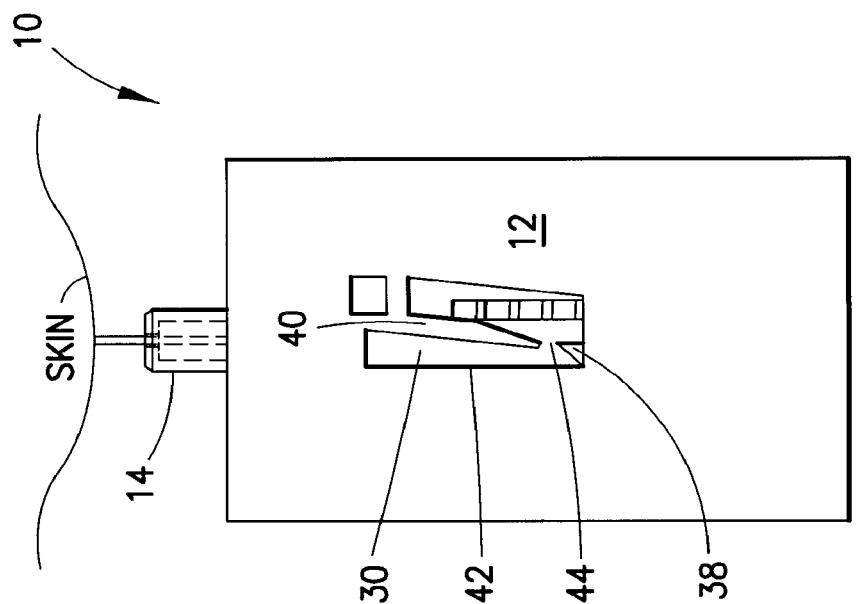
Figure 5:
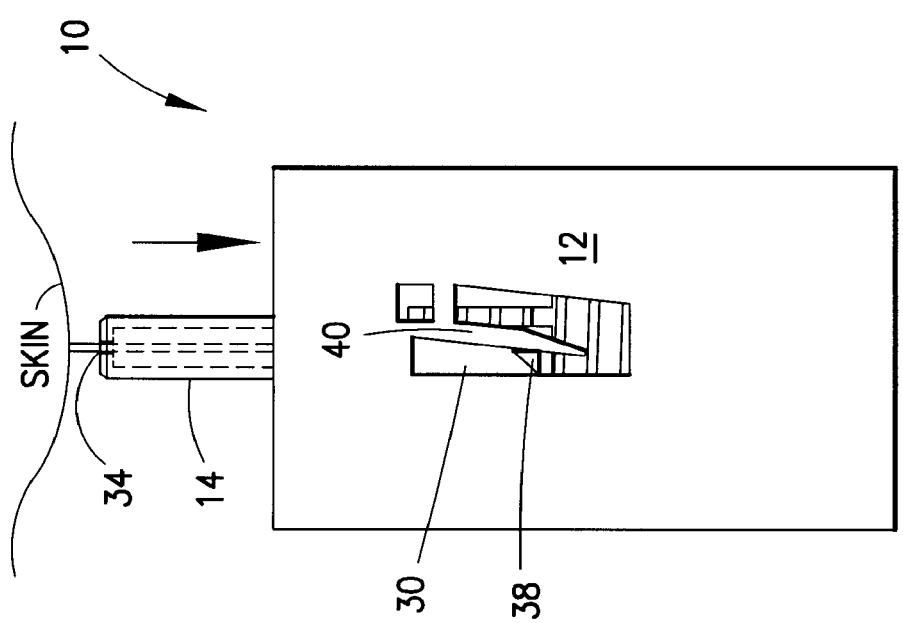

By way of non-limiting example, and with reference to FIGS. 1-8, the channel 30 is shown to have a general V-shape which permits for a locking arrangement. Specifically, a flexible finger 40 extends into the channel 30 which is inherently biased to extend towards a first edge 42 located along the channel 30. A gap 44 is defined between the flexible finger 40 and the first edge 42 which is sized to normally have a dimension smaller than the width of the protrusion 36. The gap 44 may be negligible or non-existent with the flexible finger 40 contacting the first edge 42. During use, the protrusion 38 is initially located to be in a first part 46 of the channel, which is located along the first edge 42. With the shield 14 being urged proximally, the protrusion 38 is urged proximally along the first part 46 and towards the gap 44 (FIG. 5). The protrusion 38 with sufficient proximal movement is forced through the gap 44, with the flexible finger 40 being deflected. After passage through the gap 44, the flexible finger 40 returns to its natural state (FIG. 6). The protrusion 38 passes through the gap 44 during the injection procedure (i.e., while the needle 18 is inserted into a patient the required depth for injection). In this manner, the shield 14 may be retracted to a limited depth (i.e., a depth corresponding to the protrusion 38 not passing through the gap 44) without activating the device. Once the protrusion 38 passes through the gap 44, the protrusion 38 cannot return to the initial state.

Figure 8:
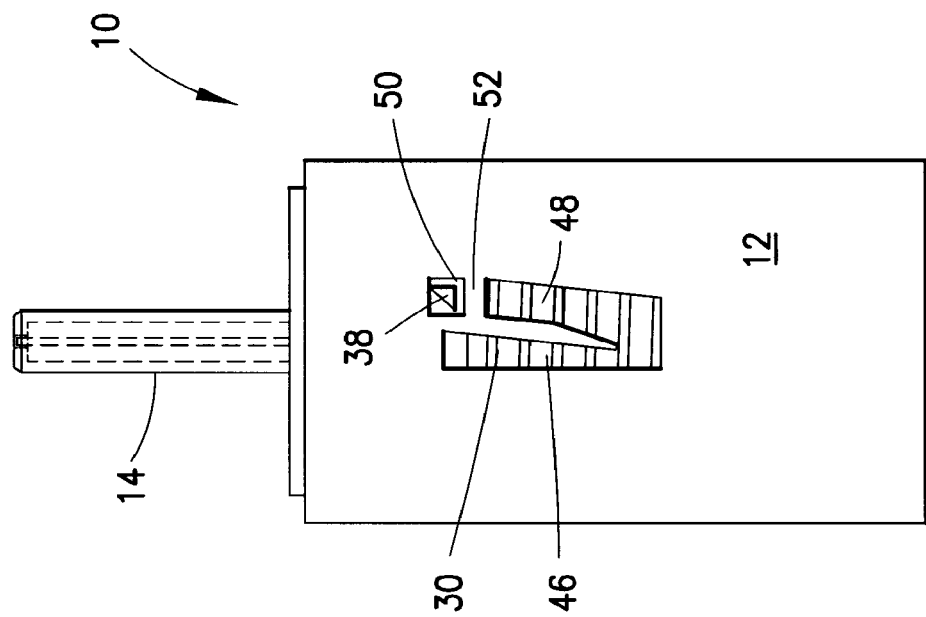
Figure 7:
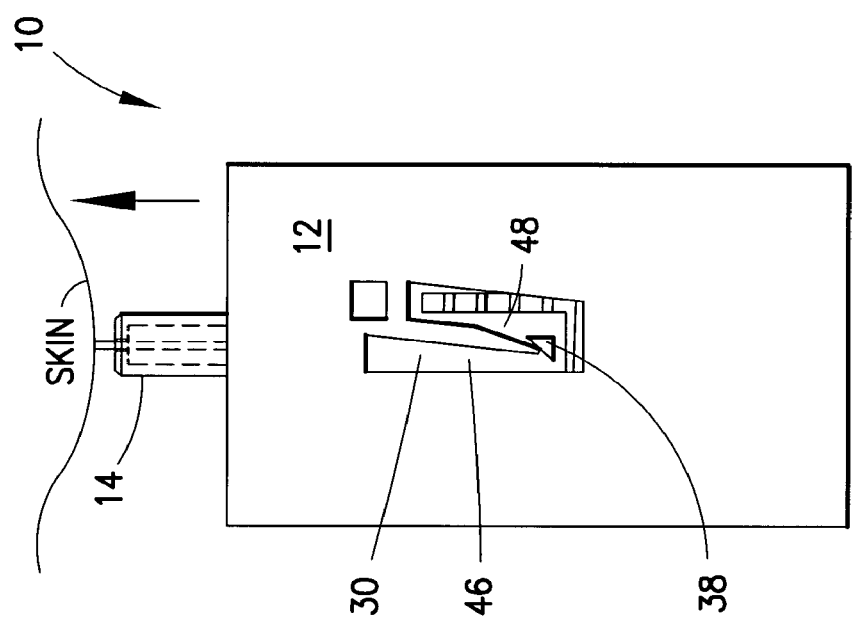
Figure 9:
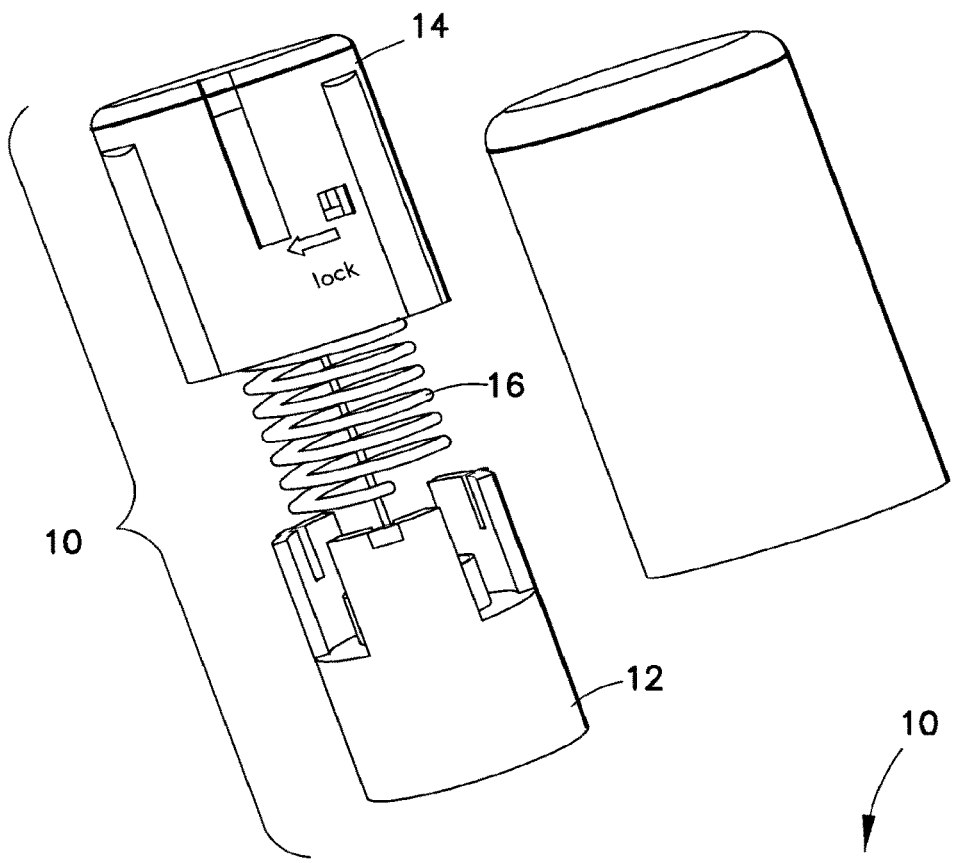
FIGS. 9-14 depict hubs or shields with straight channels that allow shields to be manually rotated to a locking position.
Figure 10:
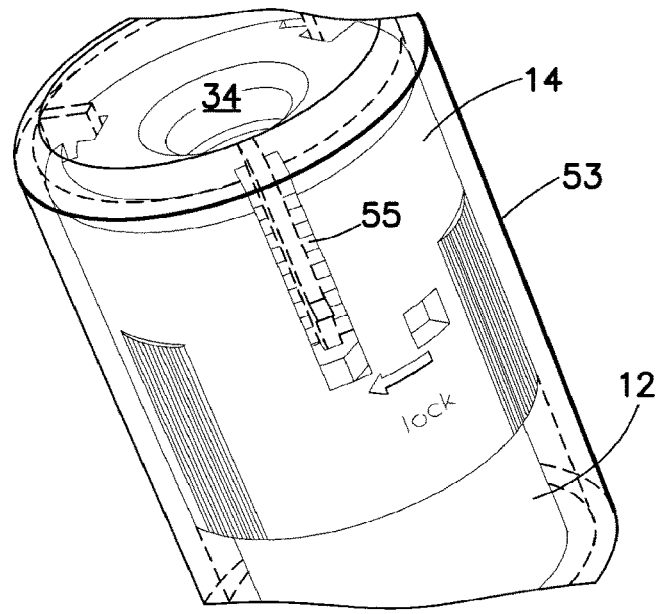
Figure 12:
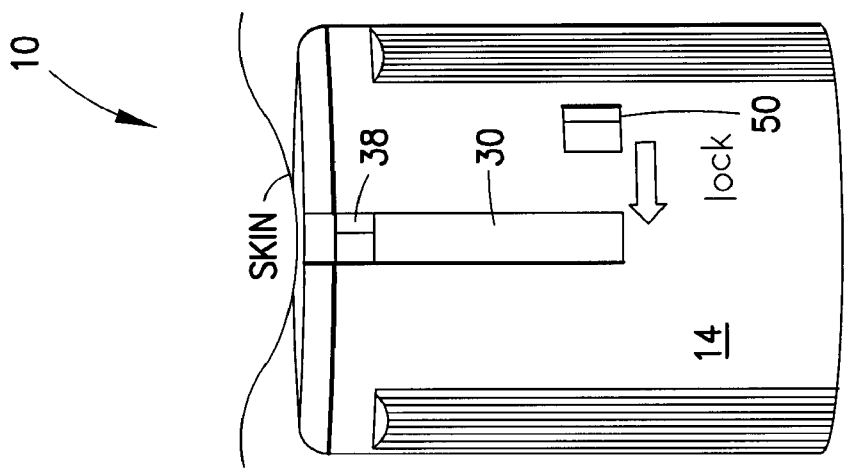
Figure 11:
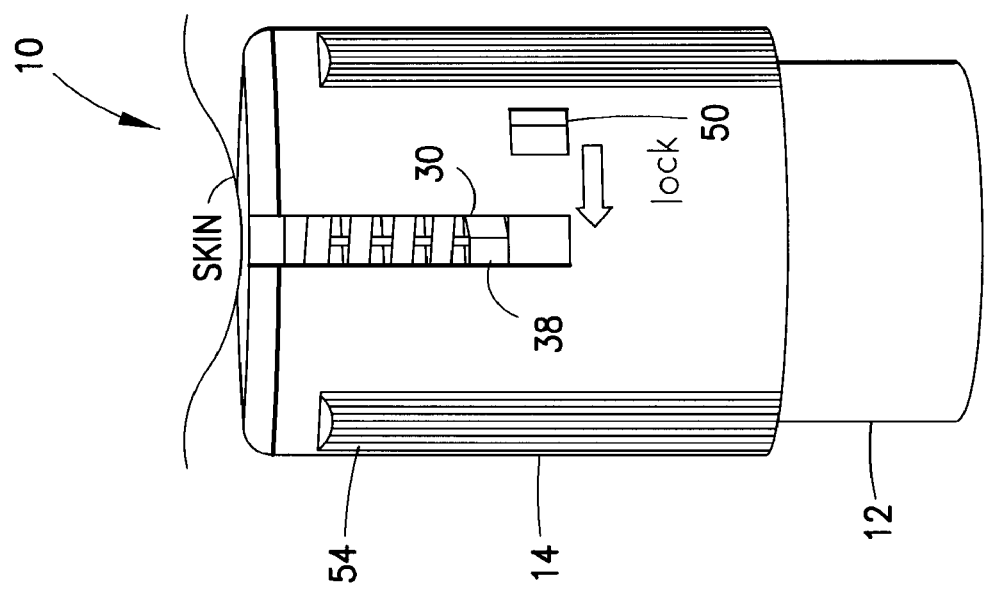
Figure 13:
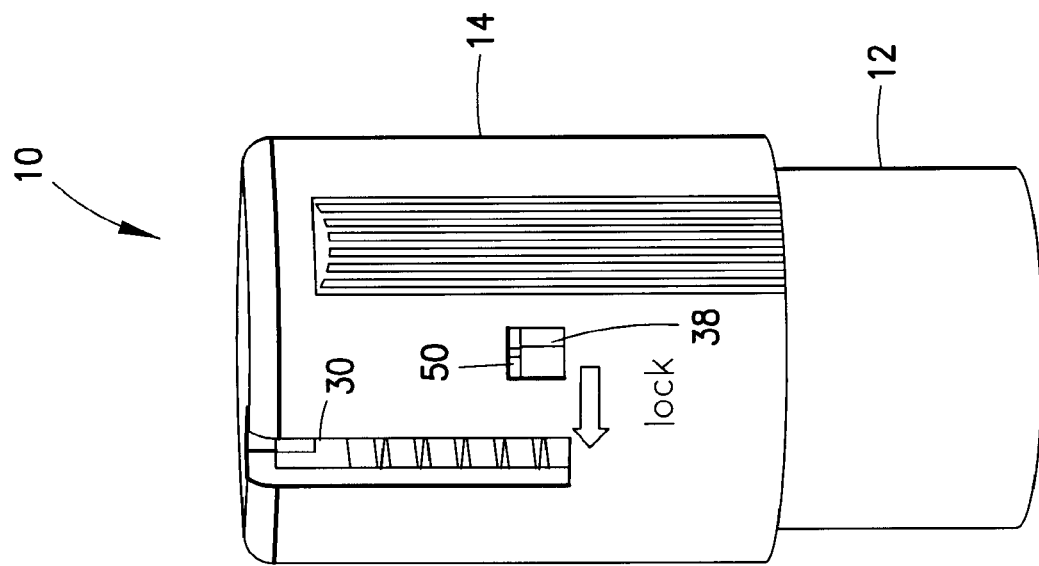
Figure 14:
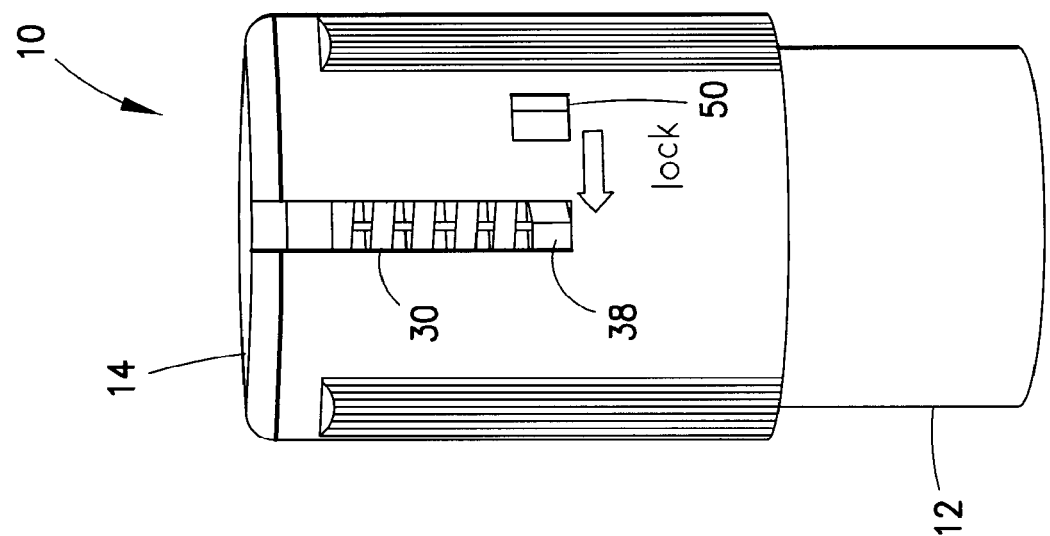

Upon the shield 14 being removed from a patient's skin, the biasing element 16 causes the shield 14 to move distally. As a result, the flexible finger 40 deflects the protrusion 38 into a second part 48 of the channel 30 (FIG. 7). To lock the shield 14 in the shielding position, a locking aperture 50 may be defined in the tubular body 24 of the hub 12 (FIG. 8). The locking aperture 50 may be located distally of the second part 48 and may be formed to receive in snap engagement the protrusion 38. Under force of the biasing element 16, with the shield 14 being completely removed from a patient's skin, the shield 14 may be urged distally with the protrusion 38 coming into snap engagement with the locking aperture 50. A ridge 52 may be defined between the second part 48 and the locking aperture 50 which inhibits the protrusion 38 from re-entering the channel 30 and allowing the shield 14 to retract proximally. The biasing element 16 must generate sufficient biasing force to urge the protrusion 38 past the ridge 52 with this arrangement. Alternatively, the protrusion 38 may be urged to a distalmost portion of the second part 48 under force of the biasing element 16, and the protrusion 38 may be then manually urged into the locking aperture 50 by forcing the shield 14 a sufficient distance to permit the protrusion 38 to snap engage the locking aperture 50. The ridge 52 may be internally ramped or curved on a proximal edge to facilitate the protrusion 38 passing thereby.

To permit the distal end 20 of the needle 18 to be initially exposed, but later fully shielded, the locking aperture 50 may be located to be more distal of the distalmost portion of the first part 46 of the channel 30, as shown in FIGS. 1-8. In this manner, in a final shielding state, the shield 14 is permitted to extend more distally from the hub 12, than in the initial state, where the protrusion 38 is received in the distalmost portion of the first part 46. Optionally, or in the alternative, the second part 48 may extend more distally than the first part 46, likewise allowing the needle 18 to be initially exposed, but later fully shielded. This may be in addition to, or as an alternative to, locating the locking aperture 50 more distal than the distalmost portion of the first part 46.

As will be appreciated by those skilled in the art, any number of protrusions 38 and the channels 30 may be used consistent with the subject invention. Likewise, any number of elements discussed with respect to the other features may likewise be used in various quantities in conjunction with the subject invention.

Further, as will be appreciated by those skilled in the art, the protrusion 38 may be formed on the hub 12 with the channel 30 being formed on the shield 14, for example, as shown in FIGS. 9-14. As such, the channel 30 may move relative to the protrusion 38. Preferably, the shield 14 is located inside of the hub 12 where the protrusion 38 is formed on the shield 14. Also, preferably, the shield 14 is located externally of the hub 12 where the protrusion 38 is located on the hub 12.

In an alternate configuration, and with reference to FIGS. 9-23, the channel 30 may be straight and parallel to a longitudinal axis of the pen needle assembly 10. The straight shape of the channel 30 allows the protrusion 38 to move back and forth, proximally and distally. Different locking arrangements are available for use with this configuration. With reference to the configuration of FIGS. 9-14, after use, the shield 14 may be manually rotated to have the protrusion 38 snap engage with the locking aperture 50.

Figure 16:
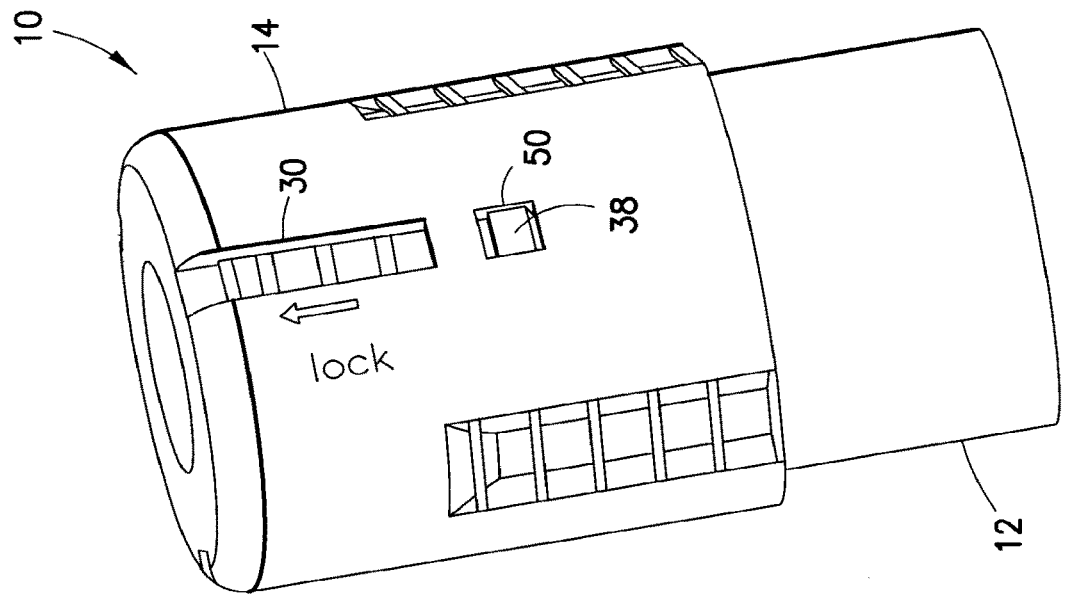
FIGS. 15-16 depict hubs or shields with straight channels that allow shields to be manually urged in a distal direction to be locked.
Figure 15:
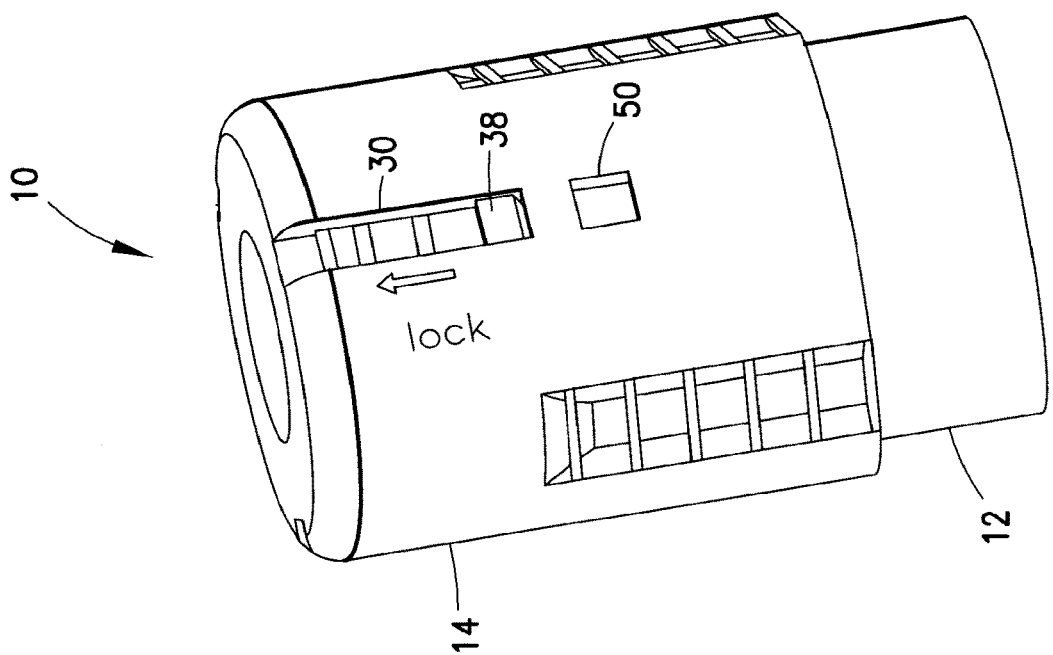
Figure 18:
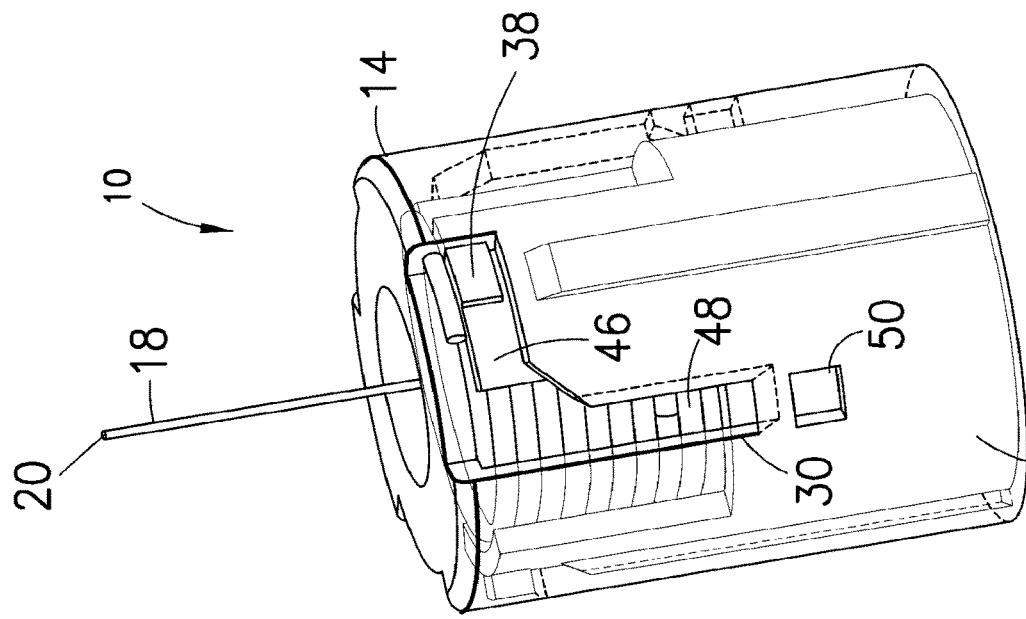
FIGS. 17-23 depict hubs or shields that allow shields to be automatically locked with a manual rotation.
Figure 17:
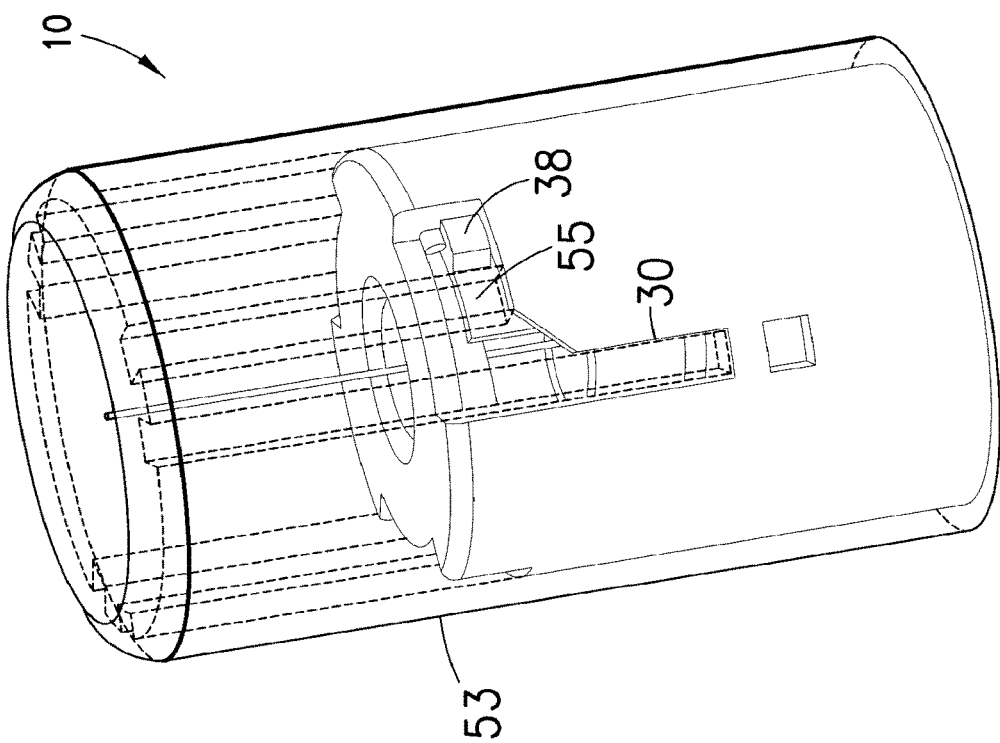

With reference to FIGS. 15-16, the locking aperture 50 may be located longitudinally spaced from the channel 30 in a proximal direction. With this arrangement, after use, the shield 14 may be urged manually in a distal direction with the protrusion 38 snap engaging the locking aperture 50.

With reference to FIGS. 9-16, the protrusion 38 may be initially seated in the channel 30 without any locking thereof. As such, the protrusion 38 may be freely movable before use. Optionally, a cover 53, having at least one inwardly extending element 55, may be provided configured to have the element 55 prevent the channel 30 from moving proximally prematurely. In addition or alternatively, the protrusion 38 may be releasably locked prior to use. For example, with reference to FIGS. 9-14, the protrusion 38 may be seated in the locking aperture 50 before use. To use the assembly 10, the shield 14 is manually rotated to urge the protrusion 38 into the channel 30. After use, reverse manual rotation of the shield 14 returns the protrusion 38 into snap engagement with the locking aperture 50.

Figure 19:
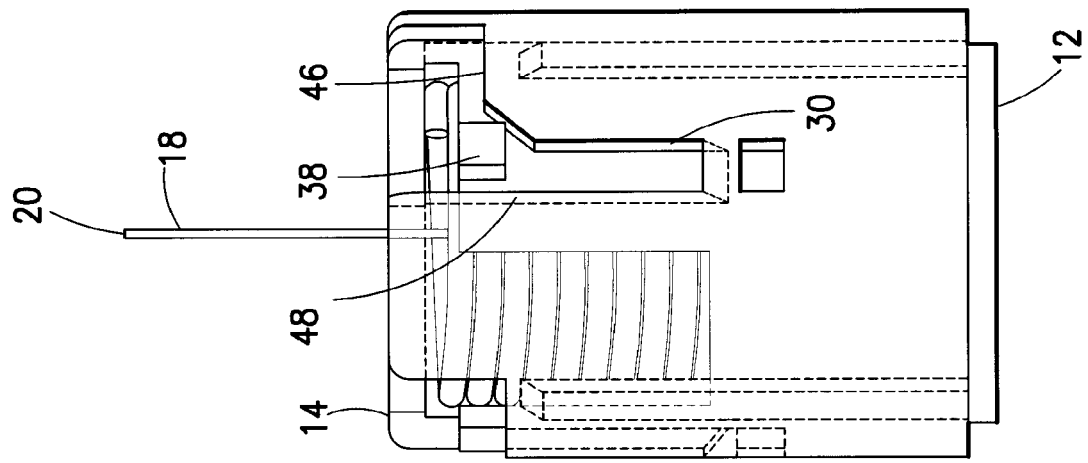
Figure 20:
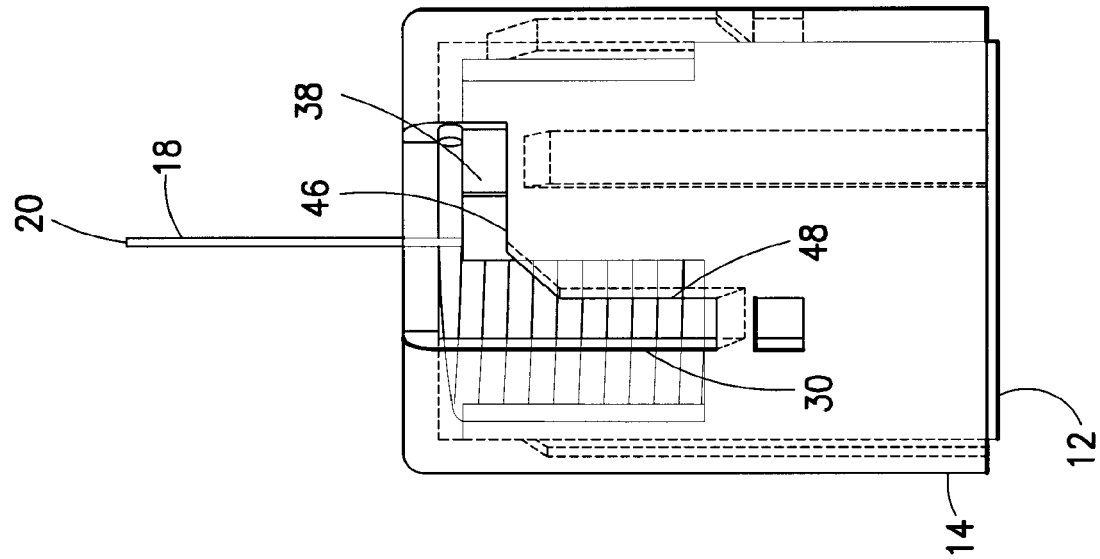
Figure 21:
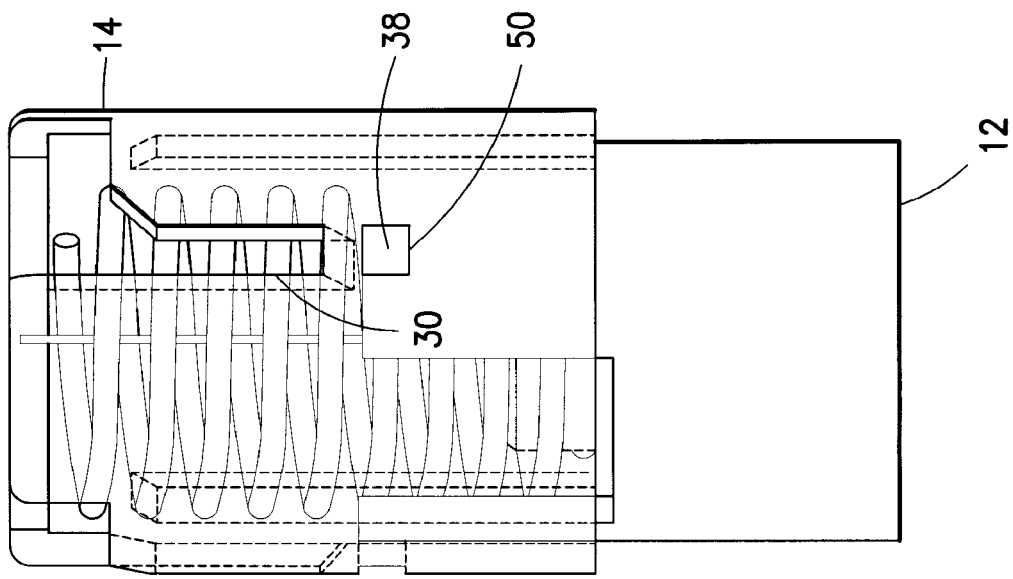
Figure 22:
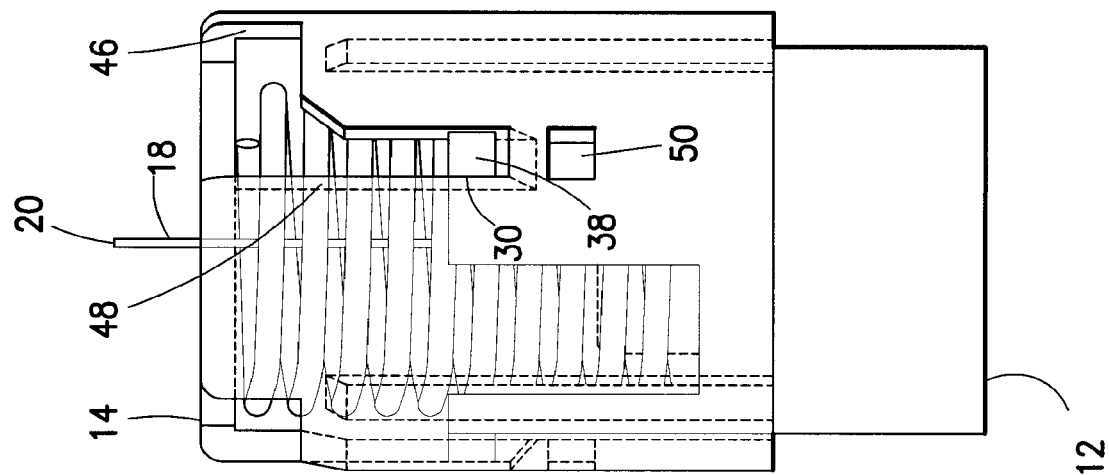
Figure 23:
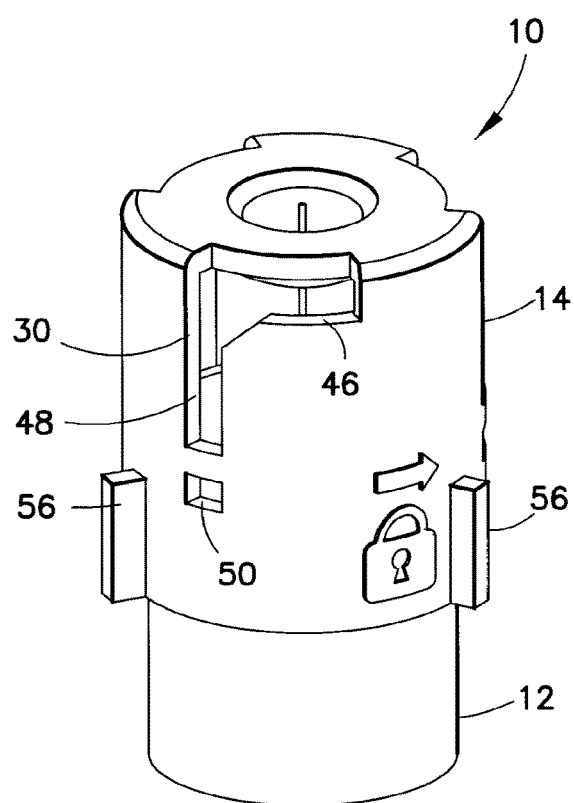

The arrangements of FIGS. 9-16 require manual intervention to achieve locking. To avoid manual locking, and with reference to FIGS. 17-23, the channel 30 may have the first part 46 disposed transversely relative to the second part 48 which is parallel to the longitudinal axis of the pen needle assembly 10. In an initial state, as shown in FIG. 19, the protrusion 38 is seated in the channel 30, particularly the first part 46, to prevent proximal or distal movement of the shield 14 relative to the hub 12. With manual rotation of the shield 14, the protrusion 38 is moved through the first part 46 of the channel 30 and into the second part 48 (FIG. 20), where the shield 14 is free to move distally under force of the biasing element 16. The biasing element 16 is selected such that sufficient force is provided to force the protrusion 38 from the channel 30 (FIG. 21) and into snap engagement with the locking aperture 50 after use (FIG. 22). Preferably, with this arrangement, the shield 14 is not rotated until the needle 18 has been removed from a patient's skin after an injection. To enhance the user's ability to rotate the shield, textured regions 54 (FIG. 11) may be provided on the tubular body 24 and/or outwardly projecting wings 56 (FIG. 23) may be provided. In addition, the cover 53 (FIG. 17), having the at least one inwardly extending element 55, may be provided configured to have the element 55 prevent the protrusion 38 from entering the second part 48 prematurely.

Figure 24:
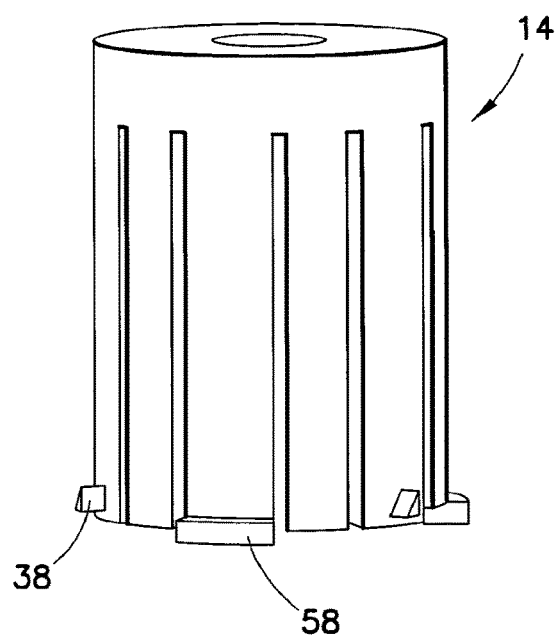
FIGS. 24-25 depict a shield with locking tabs.
Figure 25:
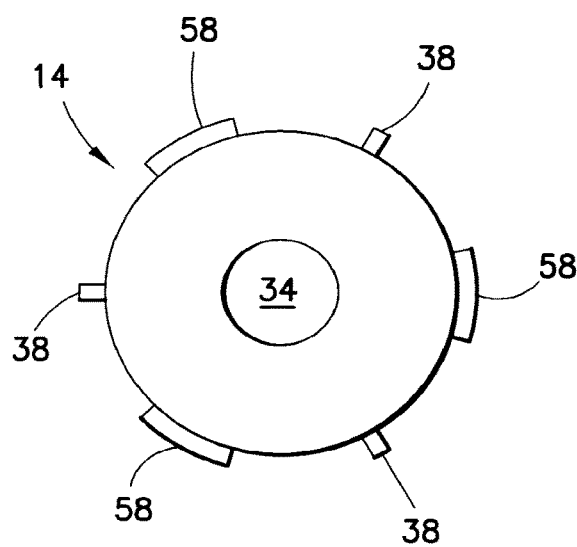
Figure 27:
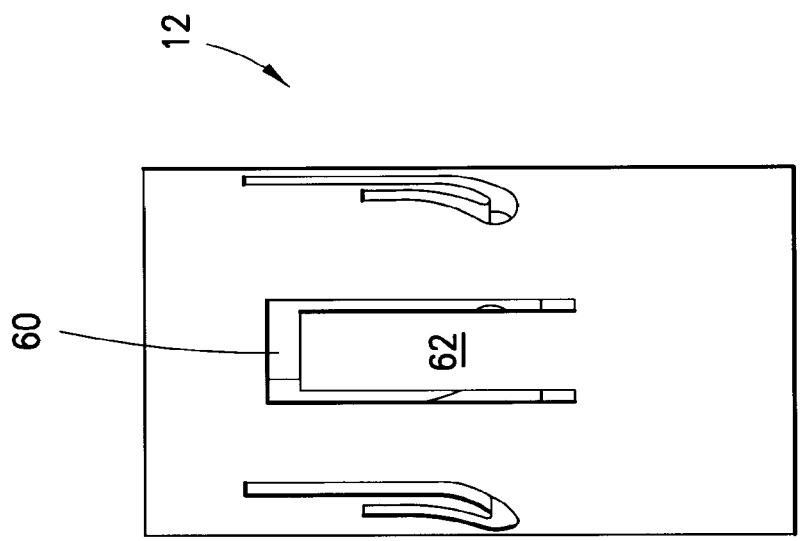
FIGS. 26-27 depict a shield or hub with a locking window and a curved channel.
Figure 26:
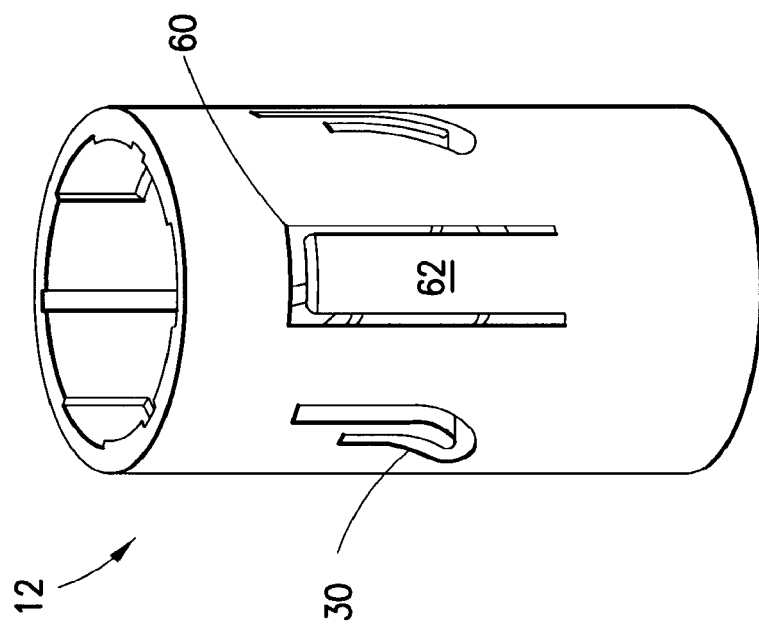
Figure 33:
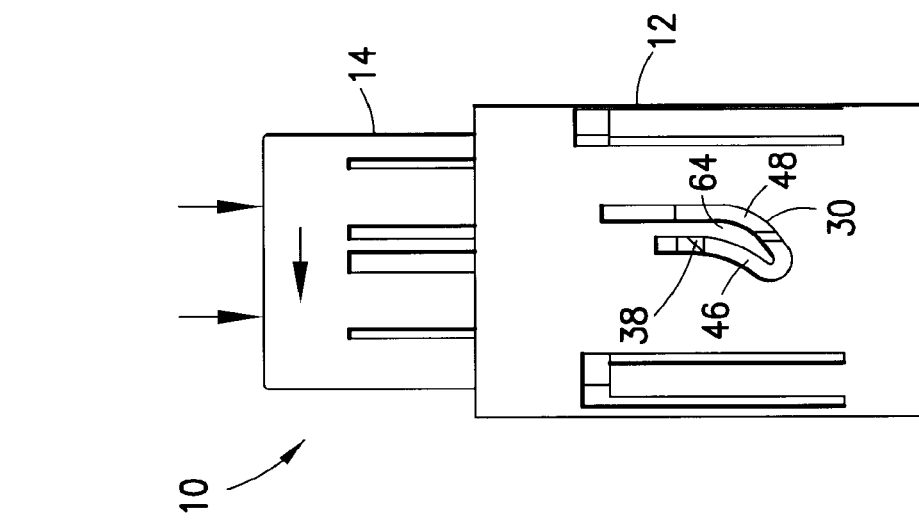
Figure 32:
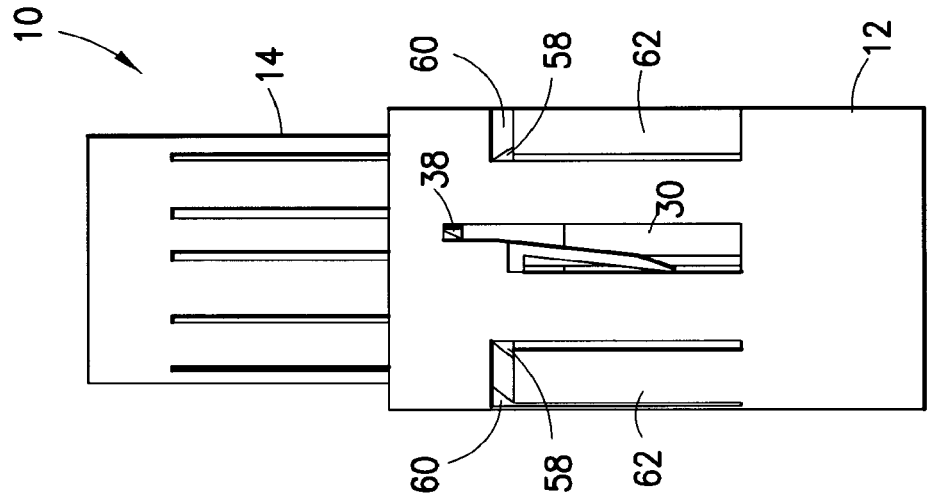
Figure 31:
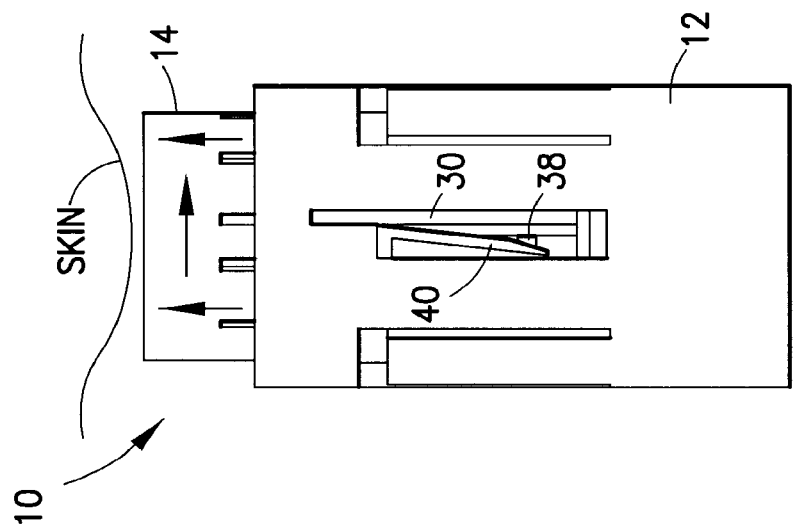
Figure 36:
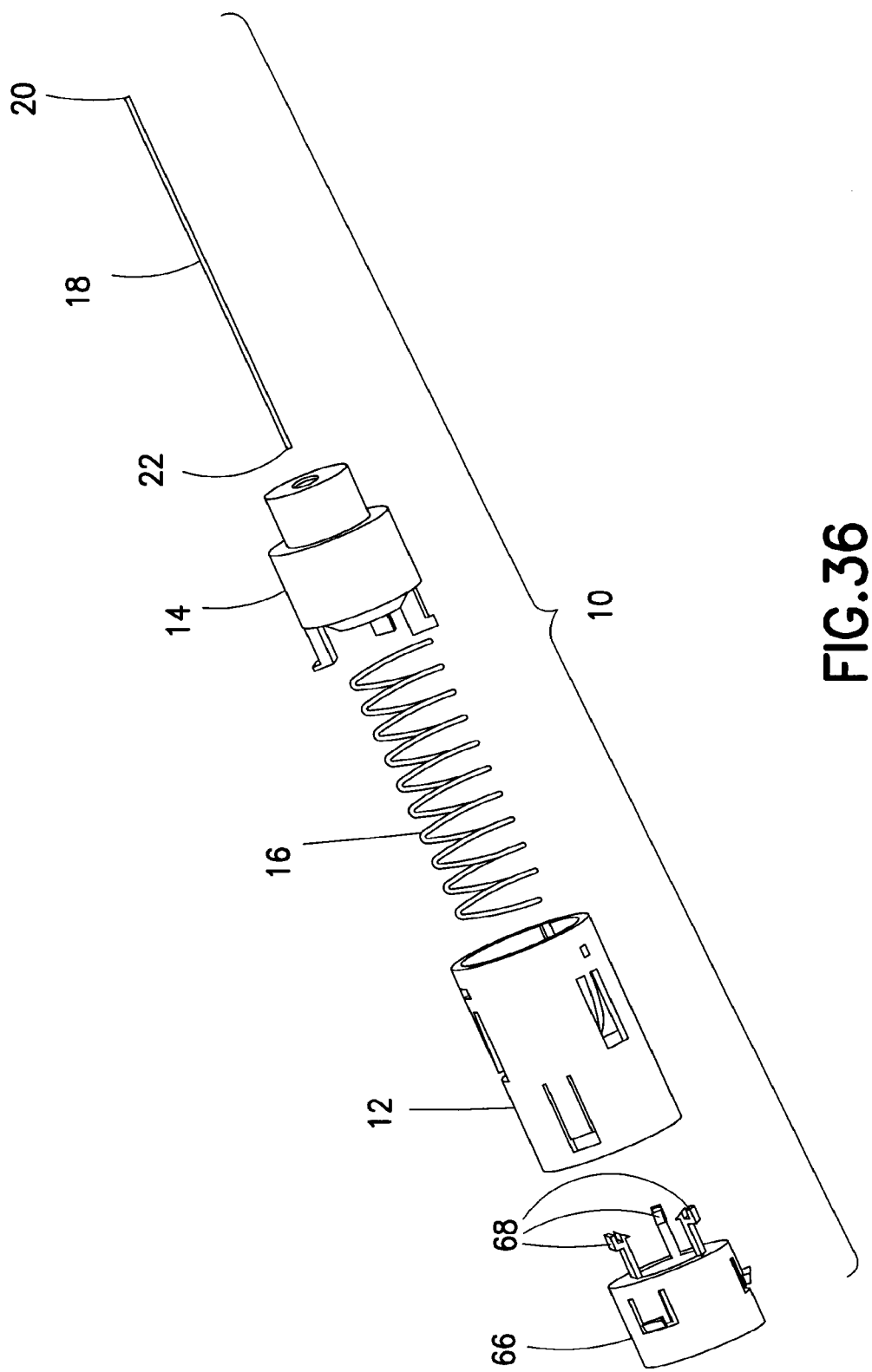
FIG. 36 depicts a safety pen assembly with a secondary shield on the proximal end.
Figure 41:
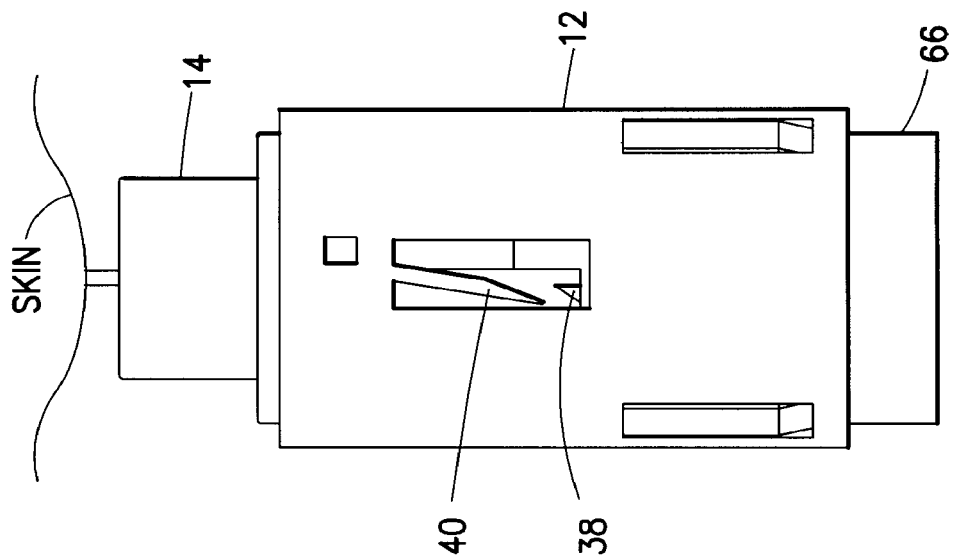
Figure 40:
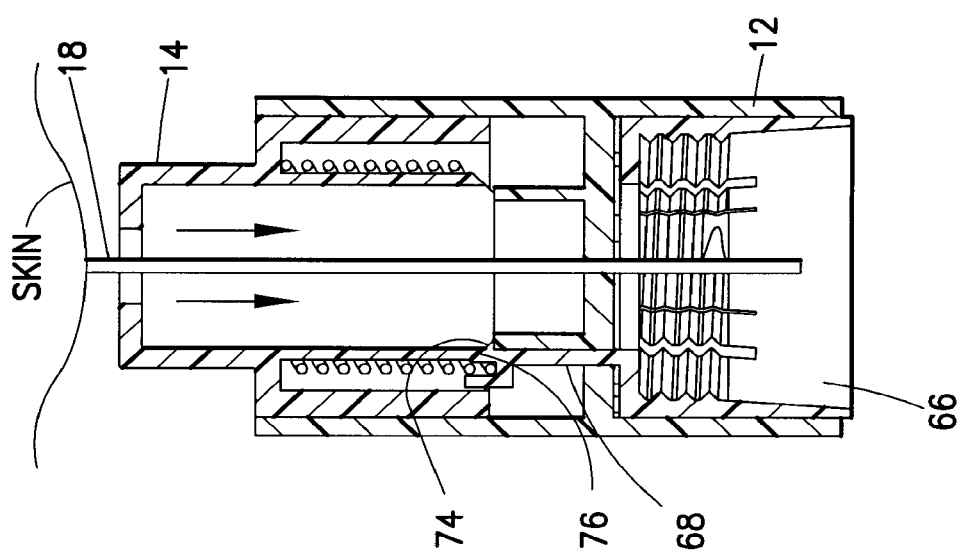

The safety pen needle assembly 10 may be configured to have an automatically rotating arrangement where the shield 14 moves rotationally relative to the hub 12, such as to achieve locking, without manual intervention beyond the normal injection procedure. With reference to FIGS. 24-25, the shield 14 may be provided with a locking tab 58 in addition to the protrusion 38. Correspondingly, locking window 60 may be formed in the tubular body 24 (FIGS. 26-27) formed to receive the locking tab 58. With reference to FIGS. 28-32, the arrangement of the channel 30, with the flexible finger 40, as described above, may be utilized. With reference to FIGS. 33-35, the protrusion 38 moving from the first part 46 to the second part 48 of the channel 30, the shield 14 is caused to rotate relative to the hub 12. With the protrusion 38 moving through the second part 48 of the channel 30, the locking tab 58 and the locking window 60 are configured such that the locking tab 58 snap engages the locking window 60 and, thus, locks the shield 14. To facilitate proper operation of this locking arrangement, cantilevered tongues 62 may be defined in the tubular body 24 proximally of the locking windows 60 to allow resilience with the locking tabs 58 traversing thereacross. As discussed above, with the second part 48 being formed longer than the first part 46, the shield 14 may permit exposure of the distal end 20 of the needle 18 prior to use (FIG. 28) with full shielding thereof after use (FIG. 32).

Figure 50:
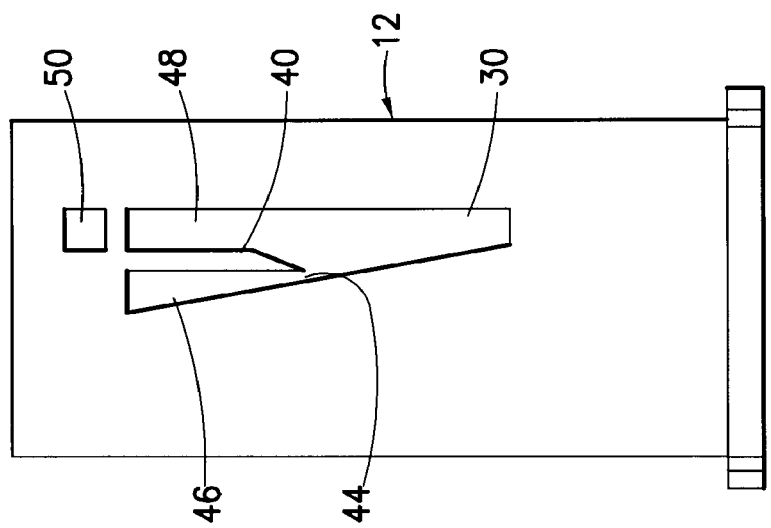
FIG. 50 depicts a hub or shield with an alternative channel design.
Figure 49:
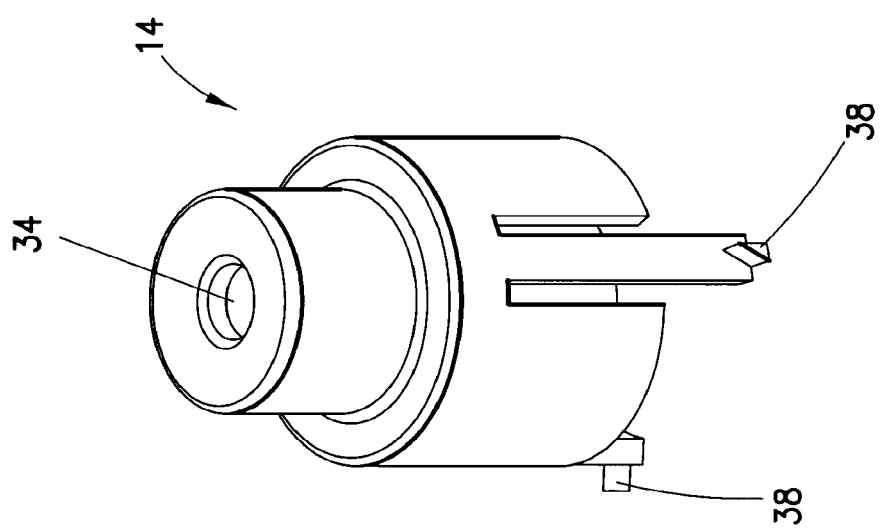
FIG. 49 depicts an alternate secondary shield for the proximal side with one or more locking arms.

As will be appreciated by those skilled in the art, the shape of the channel 30 directs the rotation of the shield 14. With reference to FIGS. 1-8, the first part 46 may be formed generally parallel to the longitudinal axis of the pen needle assembly 10. Accordingly, the shield 14 does not rotate with the protrusion 38 passing through the first part 46. Rotation is caused with the protrusion 38 passing through the second part 48, which is disposed transversely to the longitudinal axis of the pen needle assembly 10. Alternatively, as shown in FIG. 50, the first part 46 may be disposed transversely to the longitudinal axis of the pen needle assembly 10. As such, the shield 14 will rotate with the protrusion 38 traversing the first part 46—this results in the shield 14 rotating during insertion of the needle 18 into a patient. Rotation may be desired through both the first and second parts 46, 48. By angularly arranging the first and second parts 46, 48, rotation of the shield 14 may be controlled.

With reference to FIGS. 33-35, as an alternative to the flexible finger 40, the channel 30 may be provided with a stationary finger 64 separating the first part 46 from the second part 48. To ensure that the protrusion 38 moves into the second part 48 properly, it is preferred that the protrusion 38 be initially urged in the opposite direction from the desired rotational direction, while traversing the first part 46. For example, with reference to FIGS. 33-35, the stationary finger 64 is shown to be bent towards the left. As the protrusion 38 is urged proximally, the protrusion 38 also rotates to the left. In this manner, a torsional force is generated in the biasing element 16 which urges the protrusion 38 in a rightward direction. Preferably, the amount of rotation of the shield 14 (i.e., rotation of the protrusion 38) is limited during the injection. The travel of the protrusion 38 through the first part of the channel 30 coincides with the injection process. With the second part 48 being hook-shaped, once the protrusion 38 passes the stationary finger 64 and is under force of the generated torsion force, the protrusion 38 is urged into the second part 48. The protrusion 38, however, preferably does not traverse the second part 48 until after the injection, particularly after removal of the pen needle assembly 10 from the patient's skin. Upon removal of the shield 14 from the patient's skin, the biasing element 16 urges the shield 14 distally with the protrusion 38 traversing the second part 48. The locking arrangement as described above with the locking tab 58 and the locking window 60 may be utilized with this configuration.

FIG. 35A depicts an alternate arrangement for the channel 30 where the stationary finger 64 is generally straight. In this arrangement, as the pen needle assembly 10 is removed from the patient's skin, the shield 14 advances linearly through the first part 46, and the protrusion 38 contacts angular surfaces 39a, 39b, directing the protrusion 38 along the channel 30 into the second part 48. A locking arrangement may be utilized herewith such as, with angular surface 39c being provided to direct the protrusion 38 into the locking window 60. The angular surfaces 39a, 39b, 39c may be formed with straight and/or arcuate sections.

As depicted in FIGS. 51-54, a plurality of the channels 30 (30A, 30B, . . . ) and a plurality of the protrusions 38 (38A, 38B, . . . ) may be utilized. The entire circumference of the hub 12 and the shield 14 may be provided with the channels 30 and the protrusions 38.

Figure 51:
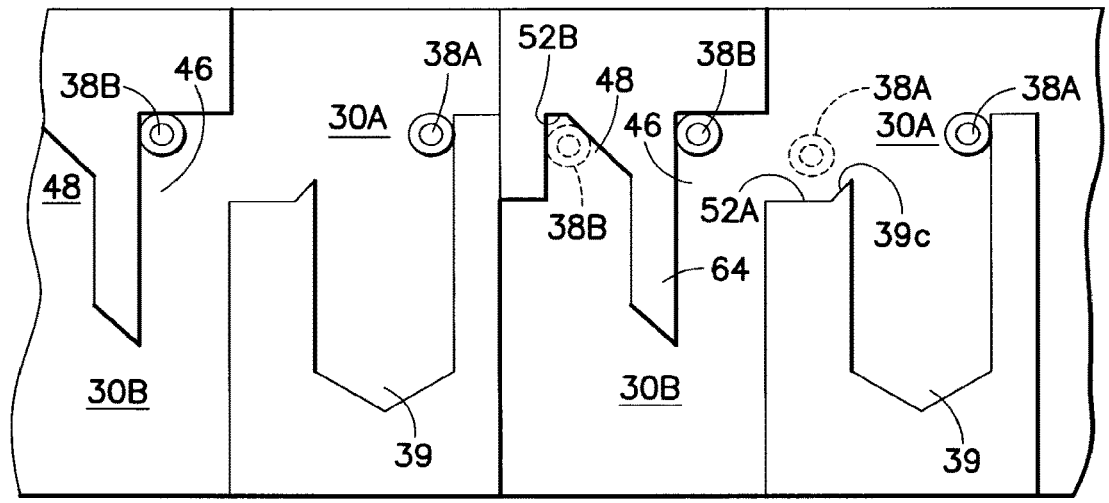
FIGS. 51-52 depicts a plurality of channels and protrusions.
Figure 52:
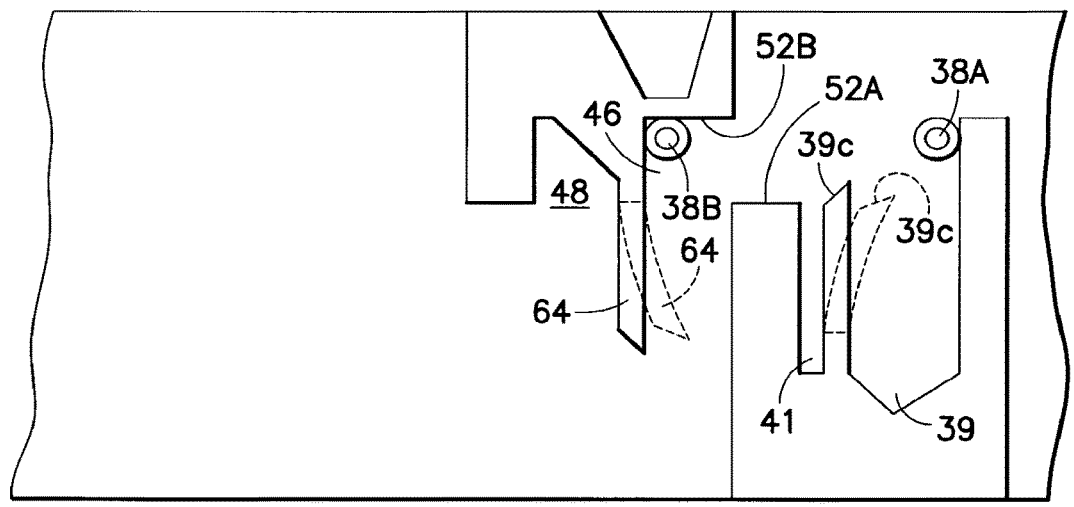

The channels 30 may be provided in a repeated pattern with like configurations. As shown in FIG. 51, the channels 30 may have different configurations, such as the channels 30A, 30B. The channel 30B includes the first part 46 and the second part 48 separated by the stationary finger 64. The first channel 30A is shown to include the first part 46 and the second part 48, with the angular surfaces 39a, 39b, but with no separating finger. With movement of the protrusion 38B about the stationary finger 64, the protrusion 38A moves simultaneously along the channel 30A. As shown in dashed lines, in a final state, the protrusions 38A, 38B are located adjacent the ridges 52 (52A, 52B). The ridges 52 are positioned so as to limit axial movement in either axial direction. For example, the protrusion 38A is located above the ridge 52A while the protrusion 38B is located below the ridge 52B. The collective effect of this arrangement is to prevent axial movement, proximally or distally.

Angled surface 39c may be provided to restrict backward movement of the protrusion 38A (and possibly movement out of a locked position). To enhance this restrictive effect, gap 41 may be defined adjacent to the angled surface 39c. Preferably, the gap 41 is smaller than the diameter of the protrusion 38A. In addition, the stationary finger 64 and/or the angled surface 39c may be defined to be deflectable, as shown in dashed lines. By being formed deflectable, the stationary finger 64 and the angled surface 39c further resist backward movement of the protrusions 38A, 38B.

In some embodiments, as set forth in FIGS. 53-54, the shield 14 may be molded with a plurality of integral protrusions 38 along the lower edge 15 of the inside diameter. If desired, the top edge of the shield 14 may be provided with a plurality of openings 43 for each protrusion 38 to facilitate formation of the protrusion 38, particularly by molding. The protrusions 38 may be incorporated as a part of a latch feature 45, which is designed to flex as it passes over tapered leads or other raised sections of the channels 30 to engage with the body of the hub 12 and be properly positioned in the channels 30 ready for use.

As will be appreciated by those skilled in the art, the safety pen needle assembly 10 may be utilized with other features, including a shielding arrangement for shielding the proximal end 22 of the needle 18 after use. With reference to FIGS. 36-49, the arrangement of the channel 30 generally discussed with respect to FIGS. 1-8 is shown. In addition, a secondary shield 66 is shown. The secondary shield 66 includes one or more locking arms 68 that pass through openings 71 of bulkhead 70 formed in the tubular body 24 of the hub 12. The locking arms 68 each include a detent 72 which latches onto a portion of the bulkhead 70 in a pre-use state. As shown in FIGS. 37-40, the proximal end 22 of the needle 18 is exposed during use.

Figure 42:
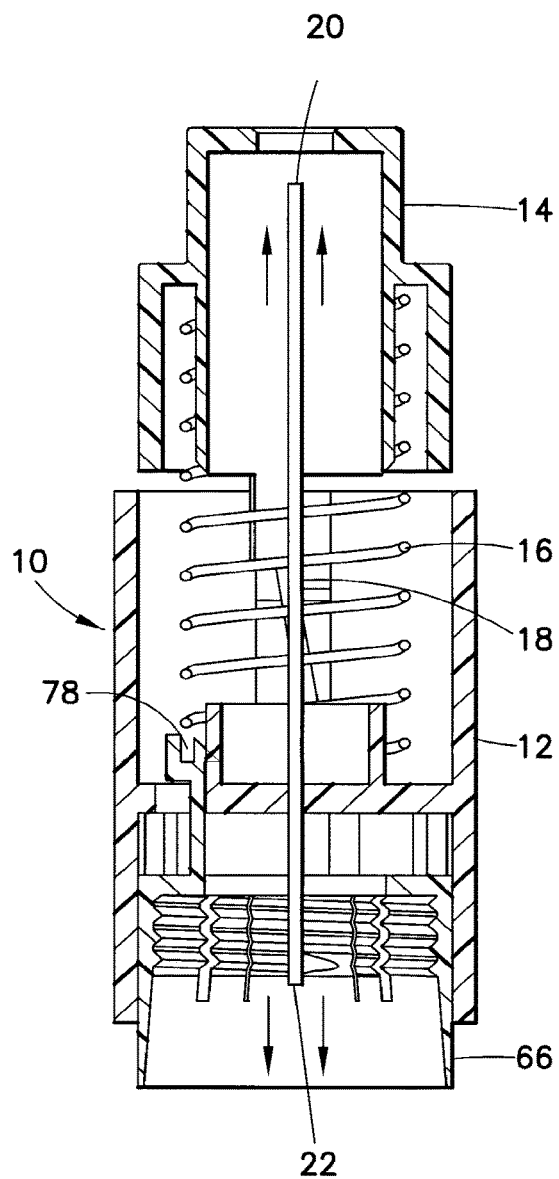
Figure 43:
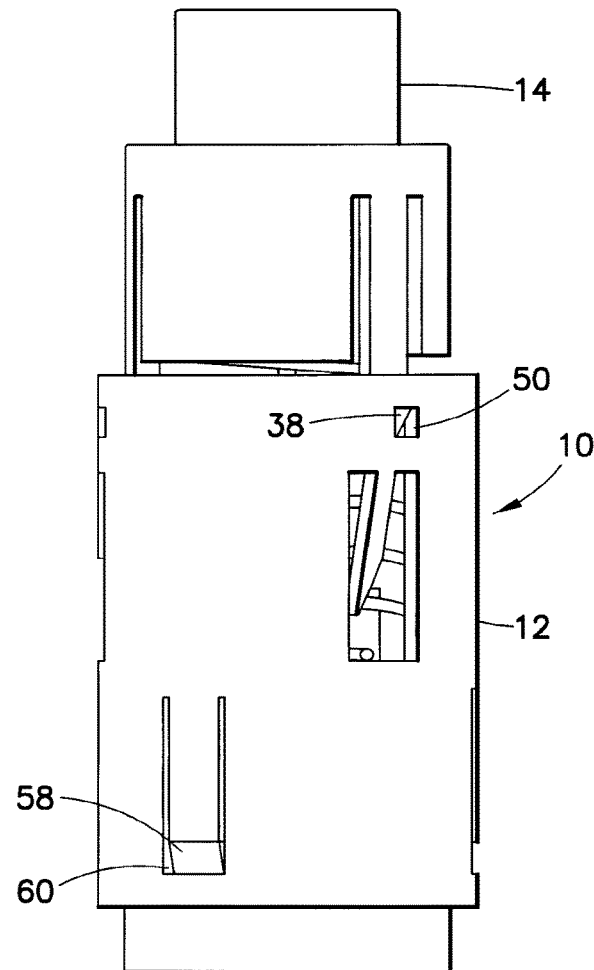
Figure 48:
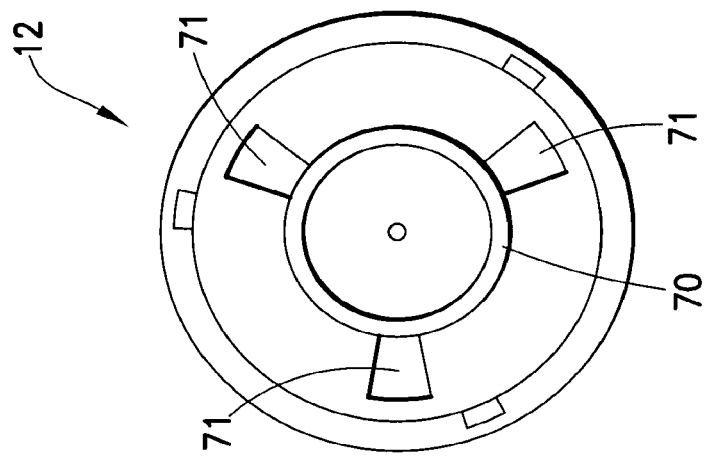
Figure 47:
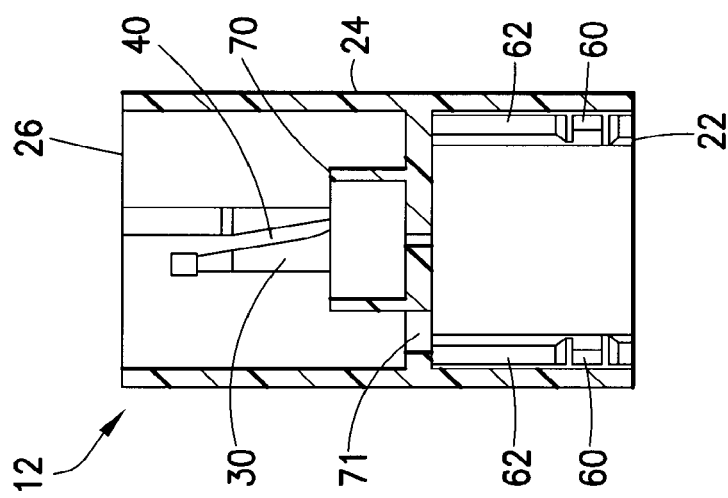
Figure 55:
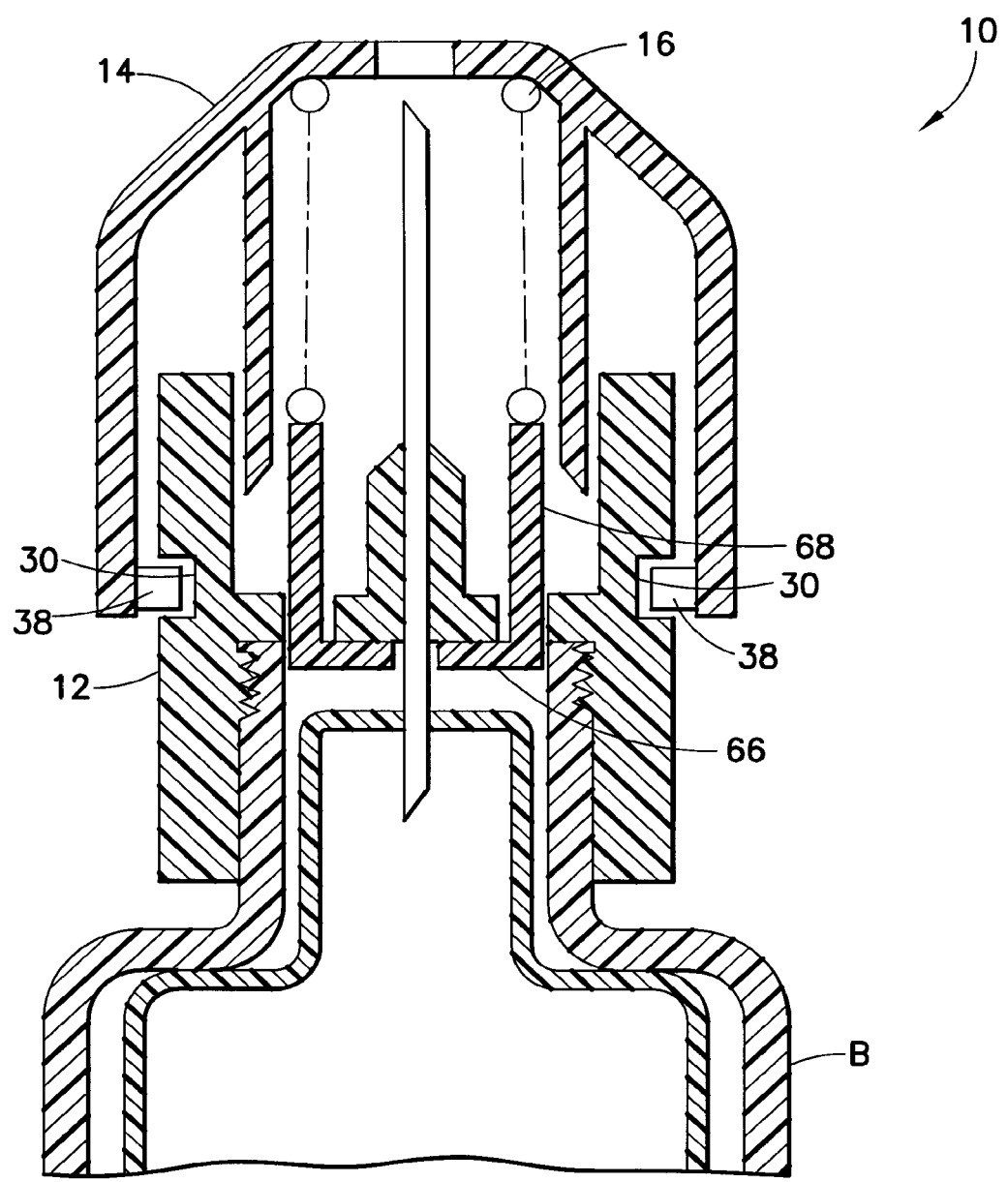
FIGS. 55-57B depict an alternative secondary shield for the proximal end.
Figure 56A:
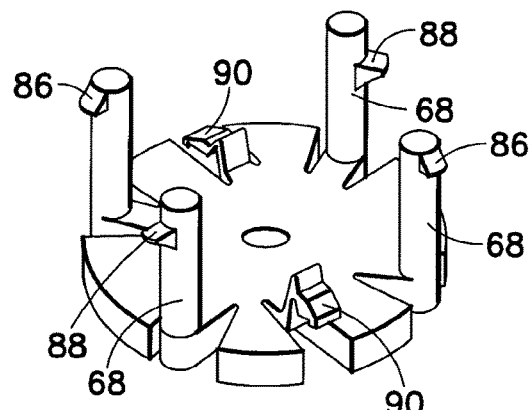

Preferably, the detent 72 includes a ramped surface 74 which faces generally distally. An angled engagement surface 76 is formed on the proximal end 36 of the shield 14 in axial alignment with the ramped surface 74. The ramped surface 74 and the engagement surface 76 are configured and arranged such that, upon sufficient proximal movement of the shield 14, the engagement surface 76 presses against the ramped surface 74 and causes outward displacement of the ramped surface 74. With sufficient outward displacement, the detent 72 unlatches from the bulkhead 70. The biasing element 16 may be located between the locking arms 68 and the shield 14 such as in a retaining channel 78. With the locking arms 68 being unlatched, the secondary shield 66 is free to move proximally under force of the biasing element 16. As shown in FIG. 42, the secondary shield 66 is urged to a shielding position where the proximal end 22 of the needle 18 is covered. The secondary shield 66 is free to move upon removal of the pen needle assembly 10 from an injector body B (FIG. 55). To lock the secondary shield 66 in this shielding position, one or more of the locking tabs 58 may be provided on the secondary shield 66 with an associated number of the locking windows 60 being formed in the tubular body 24. With the locking tabs 58 being in snap engagement with the locking windows 60, proximal or distal movement of the secondary shield 66 is limited. Alternatively, and with reference to FIGS. 55-57, the locking arms 68 may be formed with at least one secondary locking tab 86 and at least one tertiary locking tab 88. As shown in FIGS. 57A and 57B, the secondary locking tabs 86 and the tertiary locking tabs 88 are located on different locking arms 68 and spaced apart so as to sandwich the bulkhead 70 therebetween. During use, the bulkhead 70 is snap received in the collective gap formed by the secondary and tertiary locking tabs 86, 88. The secondary locking tabs 86 may be defined by the detents 72.

Figure 56B:
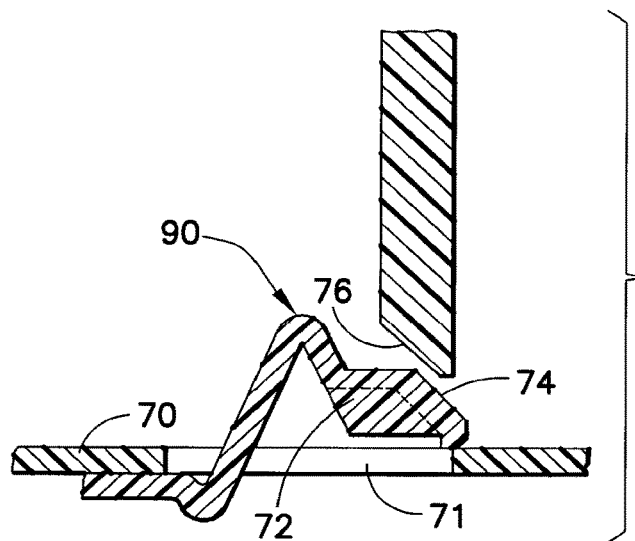

In addition, as shown in FIG. 56B, one or more latches 90 may be provided in addition to the locking arms 68 for latching the secondary shield 66 to the bulkhead 70 prior to use. The detents 72, with the ramped surfaces 74, may be formed on the latches 90, in addition, or alternatively, to the locking arms 68.

Figure 59:
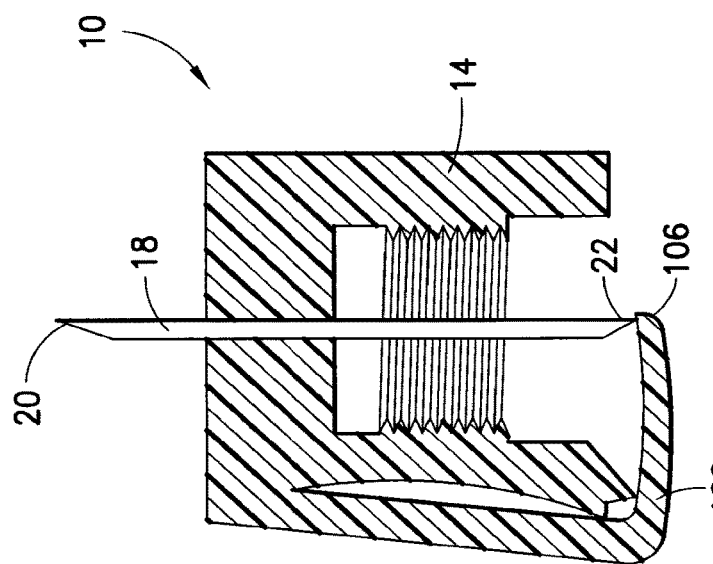
FIGS. 58-59 depict a separate embodiment for securely covering the proximal end of the needle.
Figure 58A:
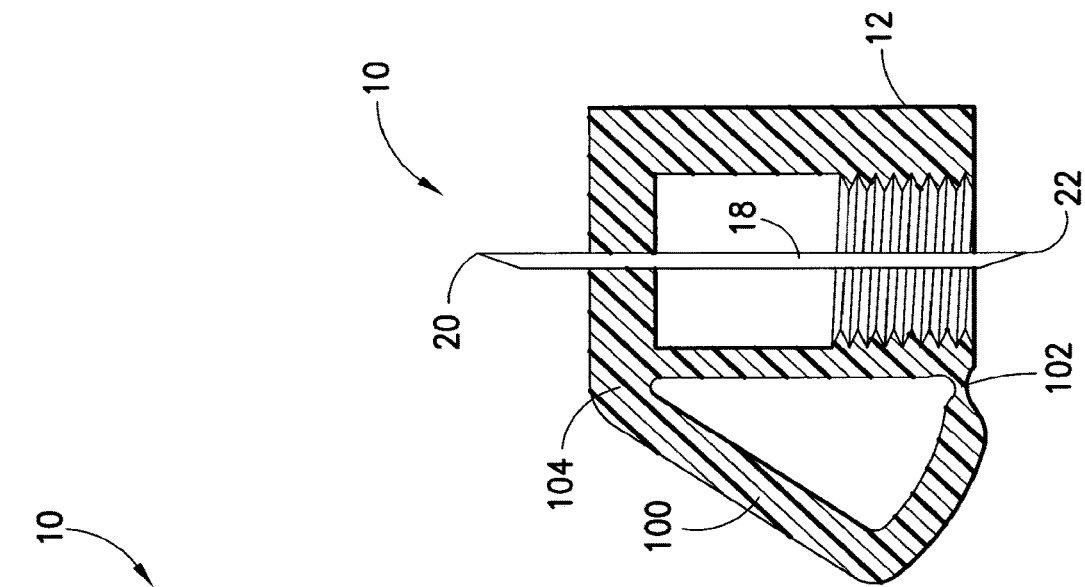
Figure 58:
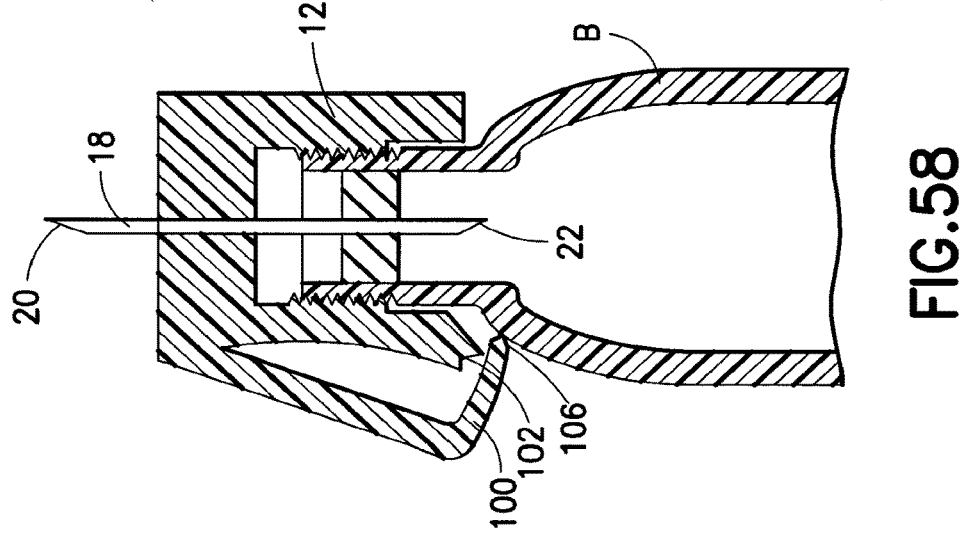

With reference to FIGS. 58a-59, a further useable shield for covering the proximal end 22 of the needle 18 is depicted. Here, a leafspring 100 is utilized which is secured to the pen needle assembly 10, preferably at the hub 12. As shown in FIG. 58a, the leafspring 100 in a pre-use state is configured to be spaced from the proximal end 22 of the needle 18. Preferably, the leafspring 100 is retained by a frangible connection 102. With reference to FIG. 58, it is preferred that the connection 102 rupture upon the pen needle assembly 10 being mounted onto the injector body B. For example, the hub 12 may be formed with a slightly smaller inner diameter, which expands upon being mounted, thus causing rupture of the connection 102.

As shown in FIG. 59, the leafspring 100 is formed with inherent memory to cover the proximal end 22 of the needle 18. Thus, with the connection 102 being ruptured, and the pen needle assembly 10 being removed from the injector body B, the leafspring 100 is free to move and shield the proximal end 22. Inherent resilience of the leafspring 100 shall cause the leafspring 100 to remain over the proximal end 22.

As will be appreciated by those skilled in the art, the leafspring 100 may be formed of various materials which provide internal resilience to urge the leafspring 100 to the shielding state. Preferably, the leafspring 100 is formed of a thermoplastic material and more preferably formed unitarily with the hub 12. Biasing force to urge the leafspring 100 to the shielding state may be generated about junction 104 formed at the intersection of the leafspring 100 and the pen needle assembly 10. Preferably, free end 106 of the leafspring 100 biases outwardly upon rupture of the connection 102 to be clear of other portions of the pen needle assembly 10. In this manner, the free end 106 is urged by the biasing force generated about the junction 104 to cover the proximal end 22 of the needle 18.

Preferably, the various locking apertures or windows discussed above for receiving in snap engagement a locking element (e.g., the locking aperture 50; the locking window 60) are preferably through holes which extend through a respective surface to permit visual confirmation of a locked arrangement from an external vantage point. The apertures or windows may be formed blind with limited depth so as to not fully extend through a respective surface. This is less desirable since visual confirmation may not be achievable. However, an audible or tactile click may be relied to indicate snap engagement.

Figure 60C:
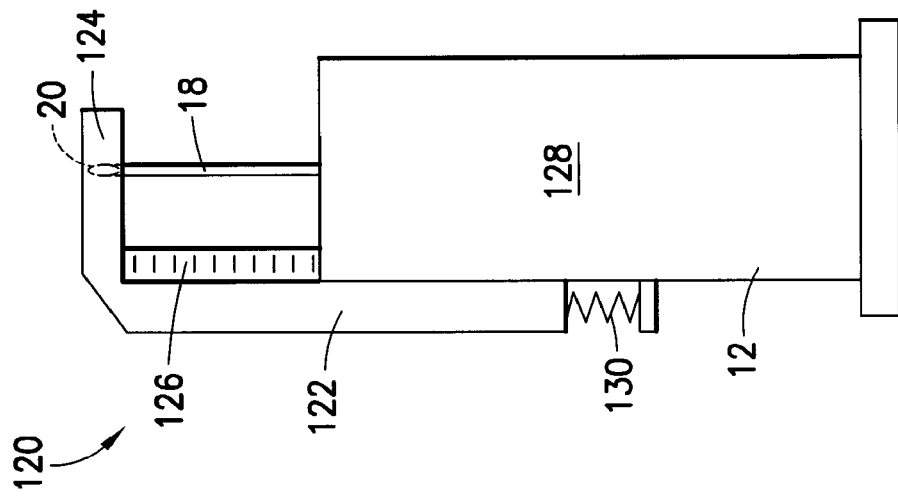
Figure 60B:
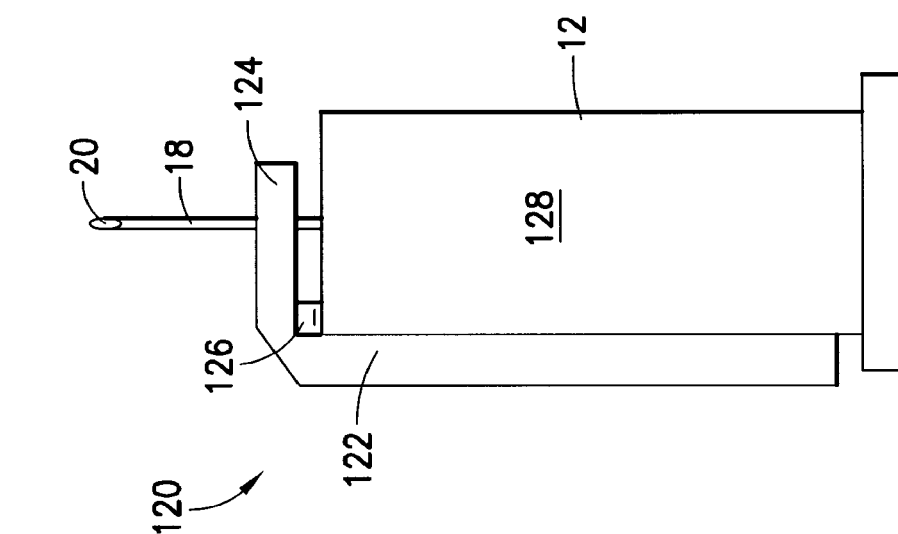
Figure 60A:
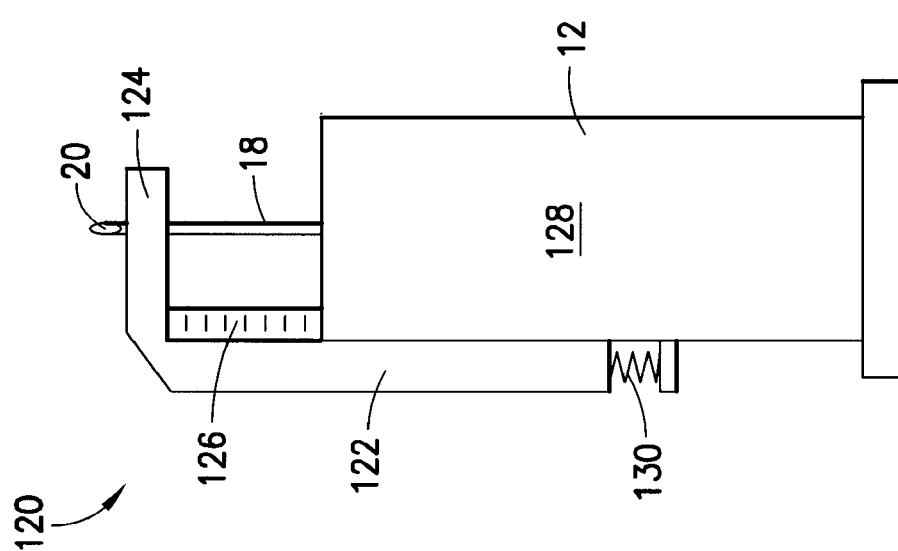

As depicted in FIGS. 60A-60C, the present invention may include one or more indicia for determining the depth of protrusion (insertion) of the needle 18 into the patient's body.

This may be important, for example, when the medication being injected is desirably administered to a particular depth into the body of the patient. The invention may include an outer shield assembly 120 that is slidably attached to the outer surface 128 of a portion of a medical injector, preferably the outer surface 128 of a needle assembly (e.g. the outer surface of the hub 12). The outer shield assembly 120 may include a small diameter cylinder 122, which is offset from the axis of the needle 18. At the top of the cylinder 122 is a shield portion 124, which may cantilever from the cylinder 122. The cylinder 122 may include one or more depth markings 126 to allow control of the insertion depth of the needle 108.

In this embodiment, as the distal end 20 of the needle 18 is inserted into the skin of the patient, the outer shield assembly 120 is pressed by a patient's skin and moved away from the distal end 20 of the needle 108 down the outer surface 128 of the assembly. As the outer shield assembly 120 is pressed down by the patient's skin, the depth markings 126 are likewise pressed down away from the distal end 110 of the needle 18. The user can thus view the depth markings 126 as the needle 18 is inserted into the skin, or after injection, and determine the proper insertion depth for the needle 18.

If desired, the outer shield assembly 120 may provide a shield for the distal end 110 of the needle 18 after use. The shield portion 124 may be formed to cover the distal end 110 of the needle 18. The shield portion 124 may be manually adjusted after use to cover the distal end 20. Preferably, the outer shield assembly 120 includes a spring 130, which biases the outer shield assembly 120 along the outer surface 128 of the assembly towards the distal end 20 of the needle 18. Prior to use, the outer shield assembly 120 may be disposed such that the distal end 20 of the needle 18 is exposed (FIG. 60A). During use, the distal end 20 of the needle 18 is pressed into the skin of the patient, thus forcing the outer shield assembly 120 down along the outer surface 128 of the assembly (FIG. 60B). Once the injection is complete, the needle 18 is removed from the skin of the patient. As the force of the skin against the outer shield assembly 120 is removed, the spring 130 forces the outer shield assembly 120 towards the distal end 20 of the needle 18, covering the tip of the distal end 20 (FIG. 60C). If desired, the outer shield assembly 120 may include a locking arrangement to secure the outer shield assembly 120 in place once it has covered the distal end 20 of the needle 18.

It will be understood by those of skill in the art that the cylinder 122 need not have a circular cross-section, rather it may be oval, ellipsoidal, or any other shape that matches up to the outer surface 128 of the assembly. For example, the cylinder 122 may be crescent shaped so as to aid in the sliding engagement with the outer surface 128 of the assembly. Further, the shield 124 need not completely surround the needle, and may include two prong-like arms that extend alongside the distal end 110 of the needle 108, preventing accidental contact.

The depth markings 126 may include a series of markings on the cylinder 122, or may include one single depth mark that is used to indicate that the needle 18 has been inserted the proper depth into the patient. Alternatively, a single depth mark may indicate that the needle 18 has been inserted a sufficient distance to engage the safety mechanism of the outer shield assembly 120 (i.e., the spring has been depressed enough to allow the shield portion 124 to cover the distal end 20 of the needle). The depth markings 126 may be etched into the cylinder 122, or they may be drawn onto the cylinder 122 with ink or any suitable material.

In an alternate embodiment, the outer shield assembly 120 may include an additional protruding member parallel to the cylinder 122 such that the outer shield assembly 120 rests along the outside of the hub. In this case, the hub may be restrained and move between the cylinder 122 and protrusions.

Figure 61:
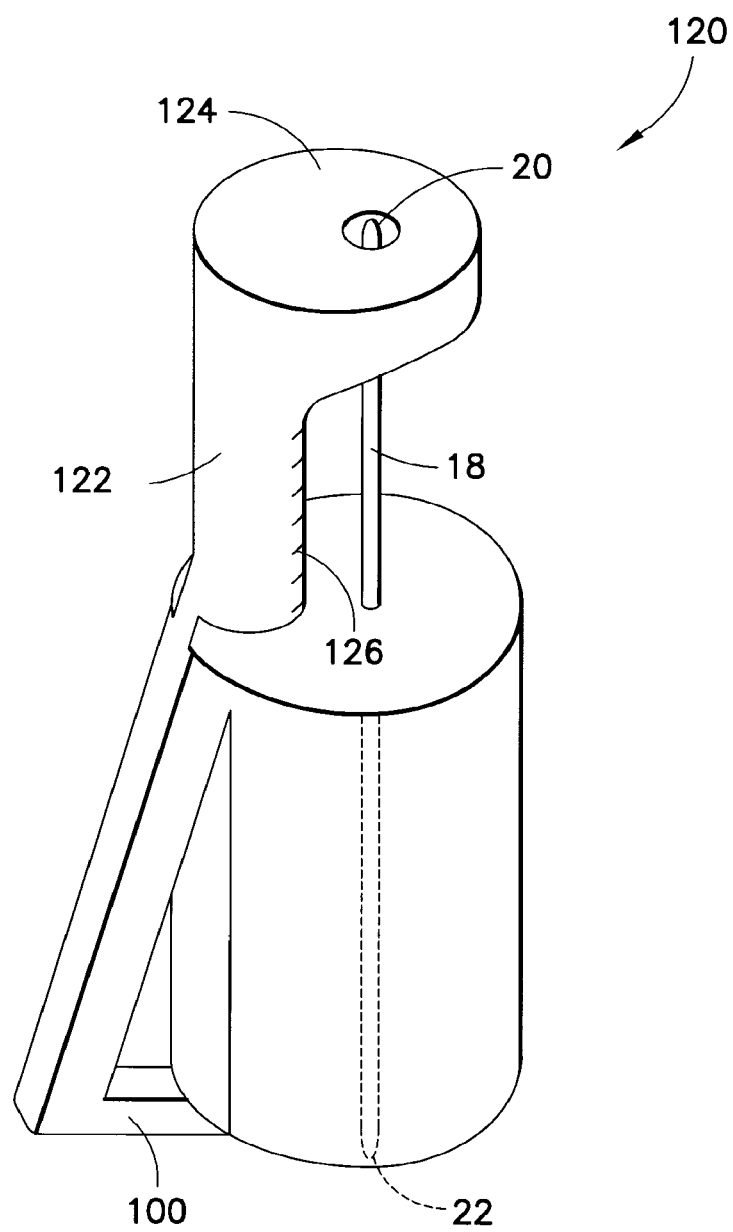

As will be appreciated by those skilled in the art, the various features described herein may be used in various combinations. For example, and with reference to FIG. 61, the non-patient shield may be used in conjunction with the depth markings and shield.

What is claimed is:

1. A safety pen assembly comprising:
   a hub;
   a needle fixed to said hub, said needle having a distal end, formed for insertion into a patient, and a proximal end; and,
   a leafspring having a first end pivotally connected to said hub, and a second end proximally located relative to said first end and secured to said hub by a frangible connection, said frangible connection being rupturable, wherein with rupture of said frangible connection, said second end is freed and urged to cover said proximal end of said needle.

2. The safety pen assembly of claim 1, wherein the leafspring and the hub are integrally formed as a unitary construction.

3. The safety pen assembly of claim 1, wherein connection of the hub to an injector body causes the rupture of the frangible connection.

4. The safety pen assembly of claim 1, wherein:
   connection of the hub to an injector body causes the rupture of the frangible connection; and
   upon rupture of the frangible connection, said second end of said leafspring displaces proximally to be clear of other portions of the hub, thereby enabling said first end of the leafspring and said hub to urge said leafspring to cover said proximal end of said needle.

5. The safety pen assembly of claim 1, wherein prior to rupture of the frangible connection, said second end is also urged to displace proximally.

* * * * *